US012471930B2

(12) United States Patent
Hyer et al.

(10) Patent No.: US 12,471,930 B2
(45) Date of Patent: Nov. 18, 2025

(54) TIBIAL ALIGNMENT GUIDE AND CUTTING SYSTEM

(71) Applicant: Implasty, LLC, Collierville, TN (US)

(72) Inventors: Christopher Hyer, Bozeman, MT (US); Thomas Roukis, Winter Garden, FL (US)

(*) Notice: Subject to any disclaimer, the term of this patent is extended or adjusted under 35 U.S.C. 154(b) by 330 days.

(21) Appl. No.: 18/170,751

(22) Filed: Feb. 17, 2023

(65) Prior Publication Data

US 2023/0263535 A1 Aug. 24, 2023

Related U.S. Application Data

(60) Provisional application No. 63/313,270, filed on Feb. 23, 2022.

(51) Int. Cl.
*A61B 17/15* (2006.01)

(52) U.S. Cl.
CPC .................................... *A61B 17/15* (2013.01)

(58) Field of Classification Search
CPC .... A61B 17/15; A61B 17/151; A61B 17/1775
See application file for complete search history.

(56) References Cited

U.S. PATENT DOCUMENTS 9,993,255 B2 * 6/2018 McGinley .......... A61B 17/1739
2021/0282790 A1 * 9/2021 Sellman ............. A61B 17/1775

* cited by examiner

*Primary Examiner* — Larry E Waggle, Jr.
(74) *Attorney, Agent, or Firm* — Brennan, Manna & Diamond, LLC

(57) ABSTRACT

The present invention relates to a patient specific instrumentation for a total ankle replacement. The system is comprised of a device primarily comprised of a device front face; a device rear face opposite the front face that may be configured to face a human tibia; a device thickness extending from the device front face to the device rear face; a device top; a device bottom that may configured to be positioned over a user's foot; a device height extending from the device top to the device bottom and perpendicular to device thickness; a device left side; a device right side; a device width extending from the device left side to the device right side and perpendicular to the device height and device thickness; and a lower portion that may include a device body.

20 Claims, 28 Drawing Sheets

TIBIAL ALIGNMENT GUIDE AND CUTTING SYSTEM

CROSS-REFERENCE TO RELATED APPLICATION

The present application claims priority to, and the benefit of, U.S. Provisional Application No. 63/313,270, which was filed on Feb. 23, 2022, and is incorporated herein by reference in its entirety.

FIELD OF THE INVENTION

The present invention relates generally to the field of patient specific instrumentation. More specifically, the present invention relates to a patient specific instrumentation for a total ankle replacement. The system is comprised of a device primarily comprised of a device front face; a device rear face opposite the front face that may be configured to face a human tibia; a device thickness extending from the device front face to the device rear face; a device top; a device bottom that may configured to be positioned over a user's foot; a device height extending from the device top to the device bottom and perpendicular to device thickness; a device left side; a device right side; a device width extending from the device left side to the device right side and perpendicular to the device height and device thickness; and a lower portion that may include a device body. Accordingly, the present disclosure makes specific reference thereto. Nonetheless, it is to be appreciated that aspects of the present invention are also equally applicable to other like applications, devices, and methods of manufacture.

BACKGROUND

More than 21,000 Total Ankle Replacements (TAR) are performed with Patient Specific Instrumentation (PSI) in the United States. However, the supposed benefits of TAR PSI such as less procedural complexity, less intra-operative radiation exposure for operating room participants, and reduced surgical time with the use of the primary TAR PSI remain unrealized. The same holds true for primary total hip, knee, and shoulder replacement. Further, the use of PSI for total hip, knee, and shoulder replacement peaked in the early 2010's and has essentially been abandoned.

Many medical professionals remain divided on the use of primary total ankle replacement (TAR) and pre-operative computed-tomography (CT) scan-based, engineer-provided plans with PSI pinning blocks. Further, said medical professionals may disagree on how to achieve optimal TAR component alignment as some medical professionals prefer standard reference guide (SRG) use while other professionals exclusively employ PSI. Furthermore, the exponential growth of TAR PSI has led to a generation of foot & ankle surgeons unable to use SRG. As a result, the US Food & Drug Administration "Manufacturer and User Facility Device Experience" describes multiple reports of TAR PSI being abandoned, wherein surgeons needed to convert to SRG in order to safely complete the TAR.

In addition, existing TAR systems lack sufficient modularity to address every patient with end-stage ankle arthritis. Further, in order to justify the time and financial costs associated with TAR PSI systems, the system must be able to demonstrate significant and consistent advantages over SRG. This is not the case with existing TAR PSI systems.

Further, the operating environment for medical procedures has changed. Historically, these procedures have been conducted in a fully operating theater in a hospital environment, which includes all of the resources that come with a hospital. However, there has been a shift to TAR surgical procedures being performed in Ambulatory Surgery Centers (ASC). The shift in part is to create efficiencies and reduce costs. However, most ASC's may not have the ability to sterilize large instrument trays on-site and many only have a mini c-arm for fluoroscopy. This is problematic, as existing TAR instrument systems are designed for full-size c-arms.

Therefore, there exists a long-felt need in the art for an improved medical device that can be used in a total ankle replacement procedure. More specifically, there exists a long-felt need in the art for a tibial alignment guide and cutting system that is sufficiently modular to account for a plurality of patient conditions during a total ankle replacement procedure. In addition, there exists a long-felt need in the art for a tibial alignment guide and cutting system that can be used with a mini c-arm during a total ankle replacement procedure.

The subject matter disclosed and claimed herein, in one embodiment thereof, comprises a tibial alignment guide and cutting system. The system is comprised of a device primarily comprised of a device front face; a device rear face opposite the front face that may be configured to face a human tibia; a device thickness extending from the device front face to the device rear face; a device top; a device bottom that may configured to be positioned over a user's foot; a device height extending from the device top to the device bottom and perpendicular to device thickness; a device left side; a device right side; a device width extending from the device left side to the device right side and perpendicular to the device height and device thickness; and a lower portion that may include a device body.

In this manner, the tibial alignment guide and cutting system of the present invention accomplishes all the forgoing objectives and provides an improved medical device that can be used in a total ankle replacement procedure that is sufficiently modular to account for a plurality of patient conditions. In addition, the device can be used with a mini c-arm. As a result, the system overcomes the limitations of existing TAR PSI systems known in the art.

SUMMARY

The following presents a simplified summary to provide a basic understanding of some aspects of the disclosed innovation. This summary is not an extensive overview, and it is not intended to identify key/critical elements or to delineate the scope thereof. Its sole purpose is to present some general concepts in a simplified form as a prelude to the more detailed description that is presented later.

The subject matter disclosed and claimed herein, in one embodiment thereof, comprises a tibial alignment guide and cutting system. The system is comprised of a device primarily comprised of a device front face; a device rear face opposite the front face that may be configured to face a human tibia; a device thickness extending from the device front face to the device rear face; a device top; a device bottom that may configured to be positioned over a user's foot; a device height extending from the device top to the device bottom and perpendicular to device thickness; a device left side; a device right side; a device width extending from the device left side to the device right side and perpendicular to the device height and device thickness; and a lower portion that may include a device body.

The device may include an upper portion comprising at least one vertical rod extending upwardly from the device body and comprising a plurality of markings. The plurality of markings are in the form of a plurality of rod holes that are 90 degrees relative to each other and spaced along the rod height. In use, the device and vertical rod may tilt slightly forwardly, 0-5 degrees (or more) forwardly or slightly rearwardly/backwardly, e.g., 0-5 degrees backwardly (or more) due to the top screw tilting the device more backward.

The device may include one or more of the following features, either alone, or in any suitable combination.

The vertical rod may be positioned in front of, for example, the tibia of a patient. The vertical rod may include a bottom end connected to the device body, a free top end forming the top of the device and a height extending from the bottom end to the free top end and parallel to the device height.

The device body includes at least one perpendicular fastener hole that extends from the front face to the rear face and perpendicular to the device width as well at least one angled fastener hole that extends from the front face to the rear face at an angle (e.g., 10 to 80 degrees) relative to the device width and inwardly. The device may include a plurality of perpendicular fastener holes that are positioned in a triangle pattern with a top perpendicular fastener hole located at the triangle apex in the center of the device width and left and right perpendicular fastener holes below the top perpendicular hole that forms the base of the triangle. Each of the perpendicular fastener holes is configured to receive at least one perpendicular fastener. In the exemplary embodiments, the device also includes at least one left-angled fastener hole and at least one right-angled fastener hole that are at approximately the same height and receive at least one angled hole fastener such that the rear ends of the angled hole fasteners may converge to allow for ease of proper positioning of the device.

The device body may further include at least one star-shaped cut-out extending from the front face to the rear face and located approximately in the center of the width. The star-shaped cut-out may include a center and at least one angled slot radiating from the center and preferably spaced at regular intervals. At least one cut-out fastener may be placed in one or more of the angled slots.

The left side and right side of the device body adjacent (i.e., at or near) the device bottom may also include at least one upwardly angled fastener hole that accommodate at least one upwardly angled fastener. The device bottom may be positioned, for example, over a user's foot. The device may include one or several cutting slots that are configured to receive a saw blade and permit cutting of bone through the cutting slots. In addition, the device may also include at least one talar cutting slot positioned below a tibial cutting slot that may extend from the front face to the rear face and that may include a talar cutting slot width parallel to the device body width and that may be configured to receive a blade of a saw so that the talus of the patient's foot may be cut through the device.

In one embodiment, the device body includes a body upper portion and a body lower portion (referred to herein as a moveable carriage) that is positioned below the device body upper portion. The device body upper portion and the moveable carriage may be connected by at least one vertically oriented left threaded bolt and at least one vertically-oriented right-threaded bolt.

The device may also include at least one angel wing that may be used to aid in positioning of the device when irradiated by x-ray. Further, in one embodiment the device may be comprised of at least one clip that functions as an outrigger structure to perform osteotomies of the fibula in conjunction with the tibia and/or talus.

Accordingly, the tibial alignment guide and cutting system of the present invention is particularly advantageous as it provides an improved medical device that can be used in a total ankle replacement procedure that is sufficiently modular to account for a plurality of patient conditions. In addition, the device can be used with a mini c-arm. As a result, the system overcomes the limitations of existing TAR PSI systems known in the art.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and are intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which.

DETAILED DESCRIPTION

Figure 1A:
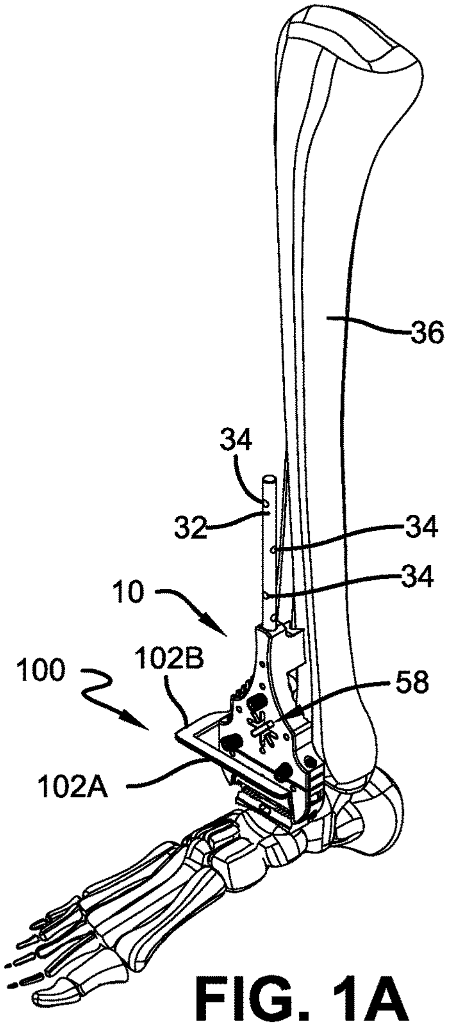
FIG. 1A illustrates a front, side perspective view of a tibial adjustment and cutting device of one embodiment of the present invention placed in front of a human tibia bone and over bones of human foot.
Figure 1B:
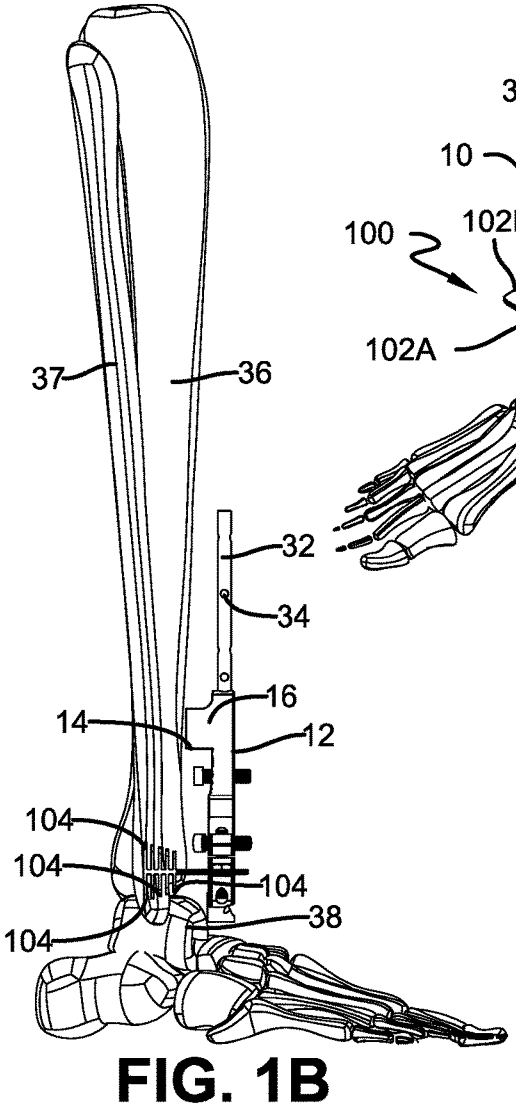
FIG. 1B illustrates a side elevation view of the device and bones of FIG. 1A, further illustrating the bottom of the middle lower prong of the angel wing positioned at the ankle joint.
Figure 1C:
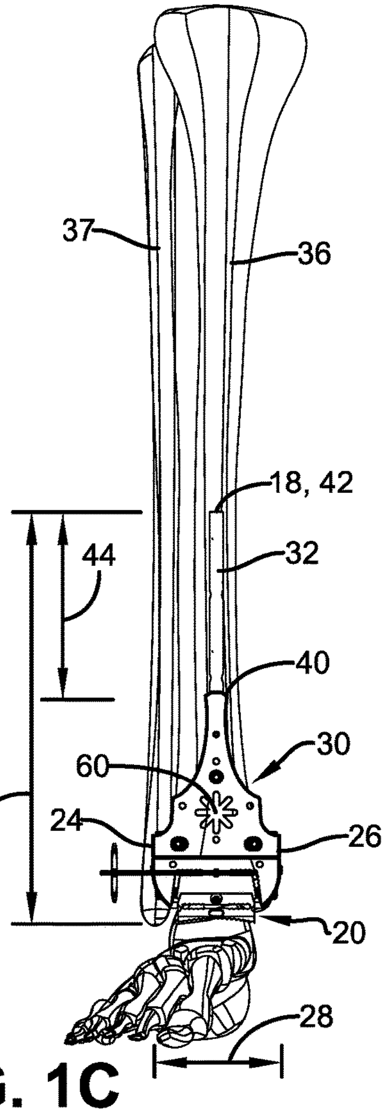
FIG. 1C illustrates a front elevation view of the device and bones of FIG. 1A.
Figure 2A:
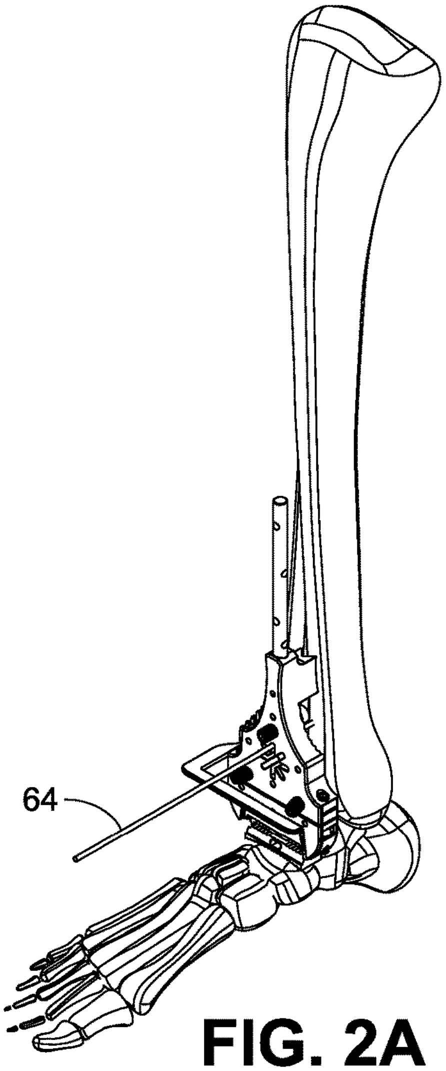
FIG. 2A illustrates a front, side perspective view of the device and bones of FIG. 1A and illustrates an exemplary step in using the device.
Figure 2B:
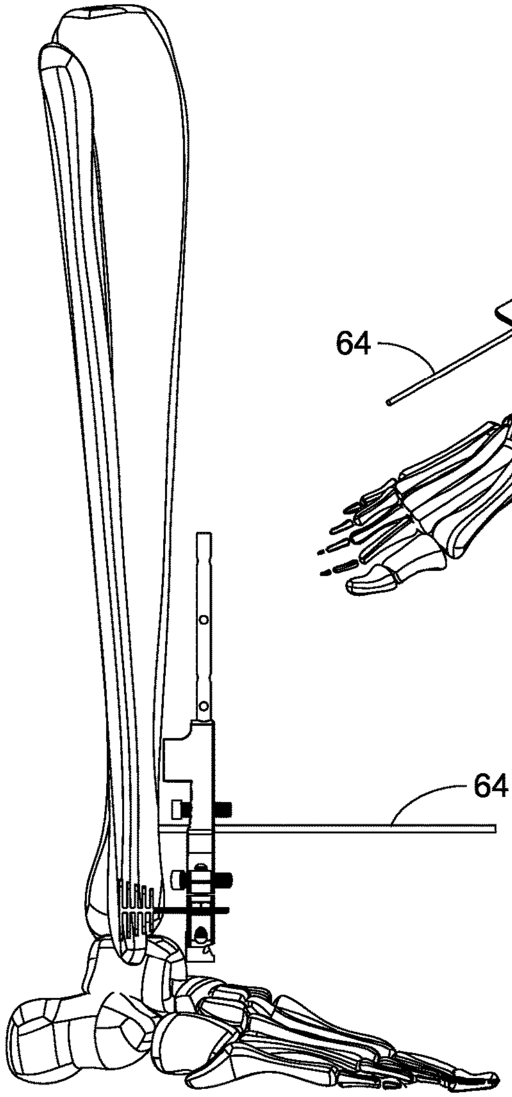
FIG. 2B illustrates a side elevation view of the device, bones, and fastener of FIG. 2A.
Figure 2C:
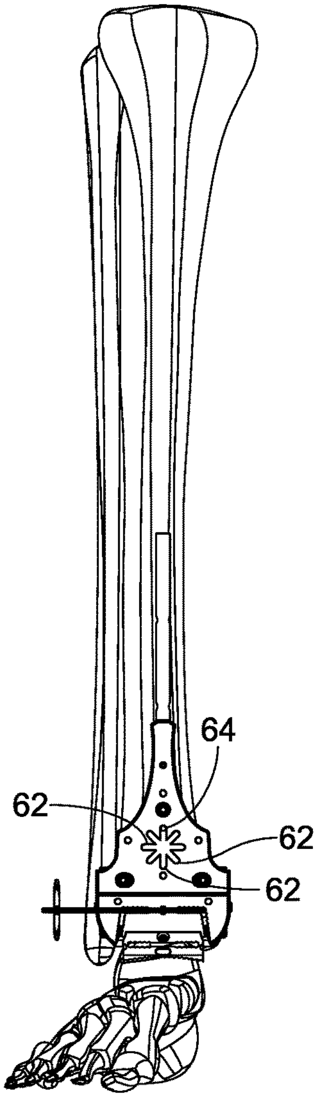
FIG. 2C illustrates a front elevation view of the device, bones and fastener of FIG. 2A.
Figure 3A:
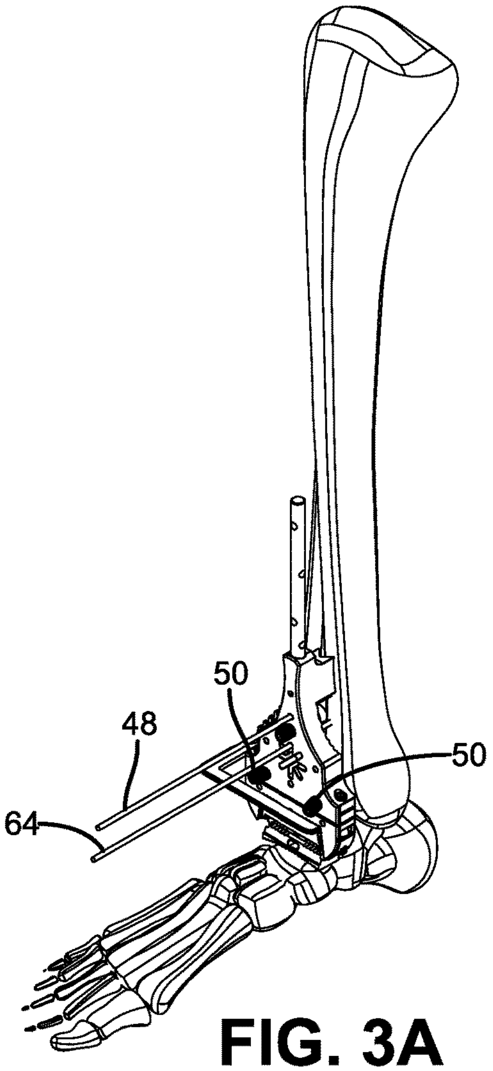
FIG. 3A illustrates a front, side perspective view of the device, bones and fastener of FIG. 2A and illustrates an exemplary step in using the device.
Figure 3B:
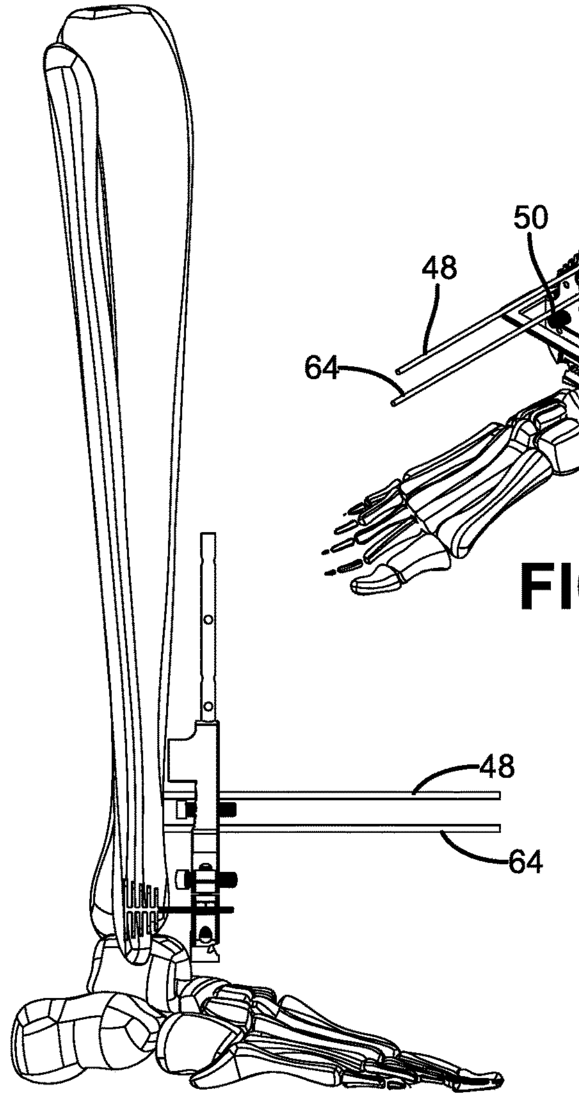
FIG. 3B illustrates a side elevation view of the device, bones, and fasteners of FIG. 3A.
Figure 3C:
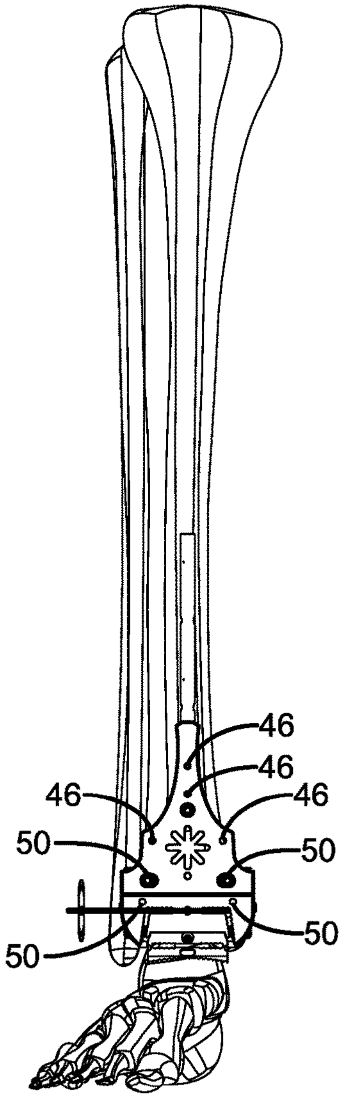
FIG. 3C illustrates a front elevation view of the device, and bones and fasteners of FIG. 3A.
Figure 4A:
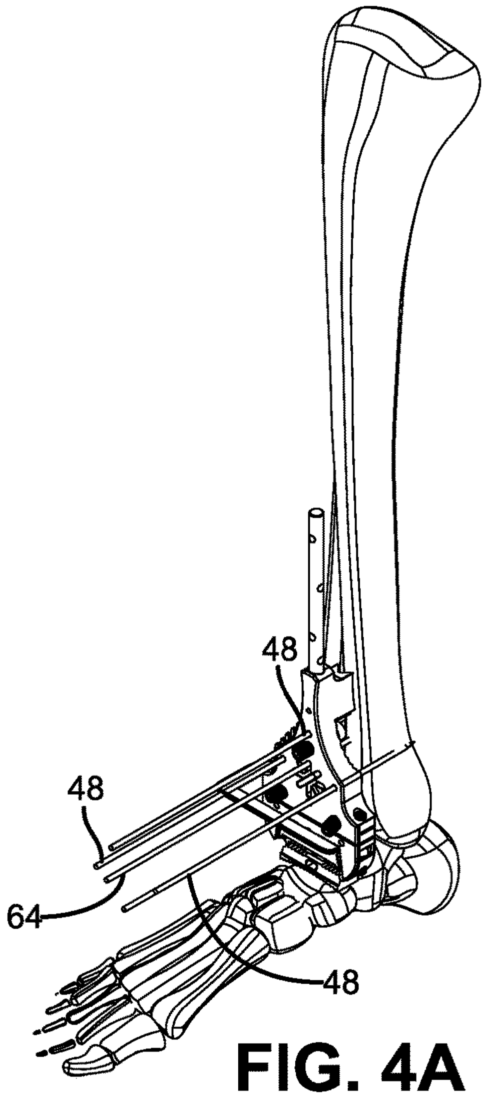
FIG. 4A illustrates a front, side perspective view of the device, bones and fasteners of FIG. 3A and illustrates an exemplary step in using the device.
Figure 4B:
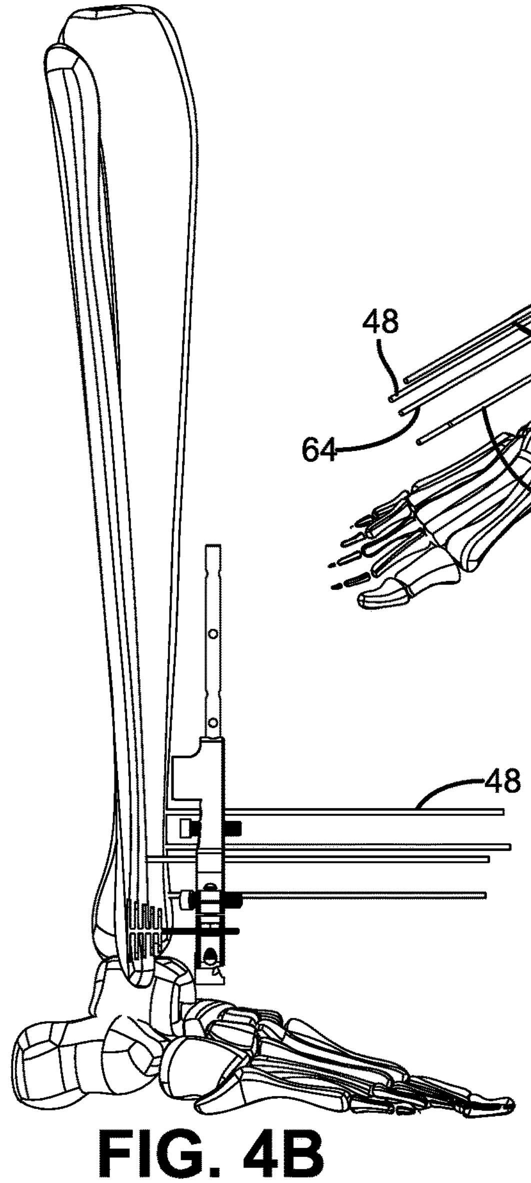
FIG. 4B illustrates a side elevation view of the device, bones, and fasteners of FIG. 4A.
Figure 4C:
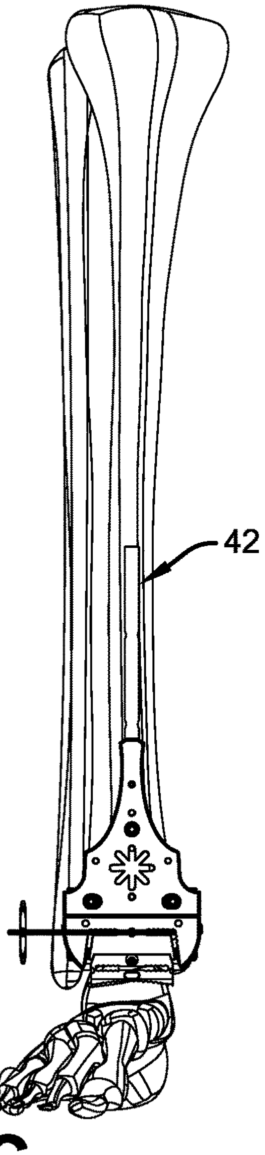
FIG. 4C illustrates a front elevation view of the device, and bones and fasteners of FIG. 4A.
Figure 5A:
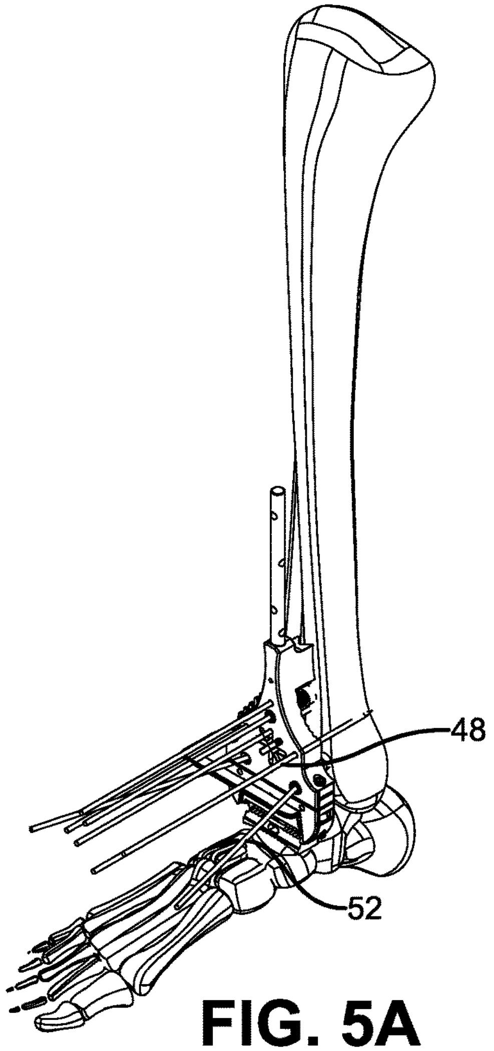
FIG. 5A illustrates a front, side perspective view of the device, bones and fasteners of FIG. 4A and illustrates an exemplary step in using the device.
Figure 5B:
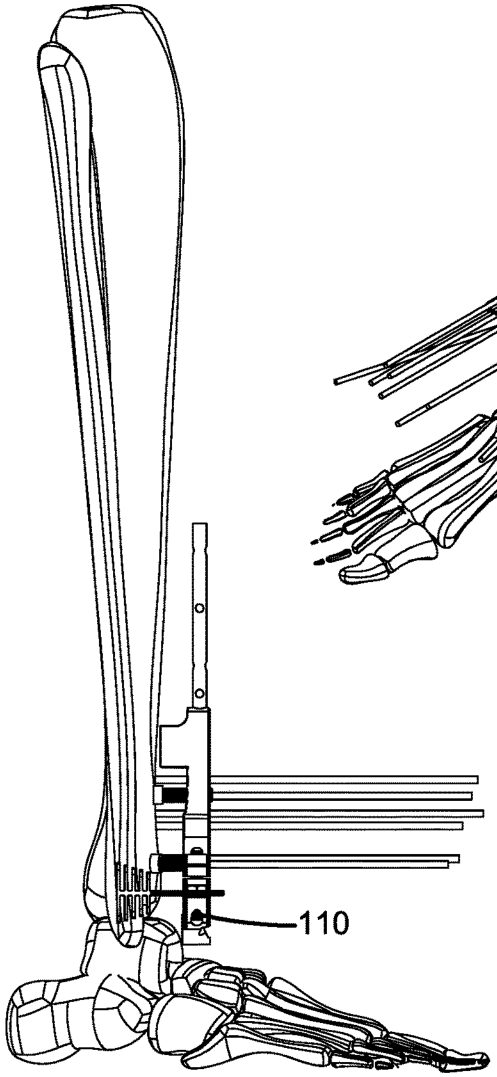
FIG. 5B illustrates a side elevation view of the device, bones, and fasteners of FIG. 5A.
Figure 5C:
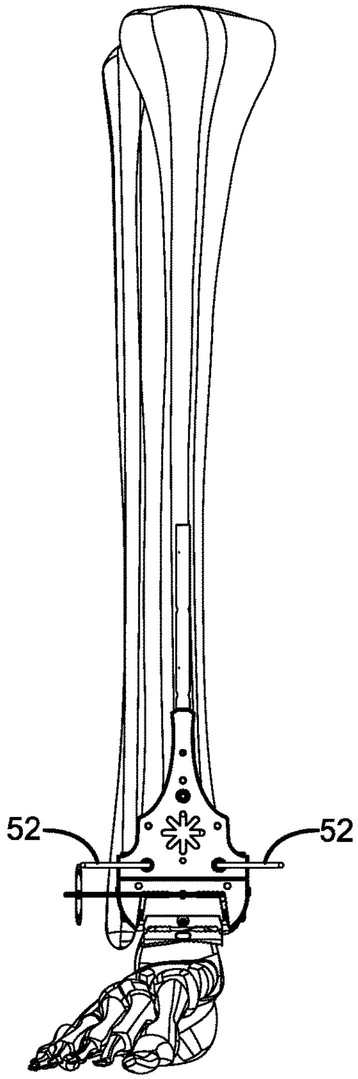
FIG. 5C illustrates a front elevation view of the device, and bones and fasteners of FIG. 5A.
Figure 6A:
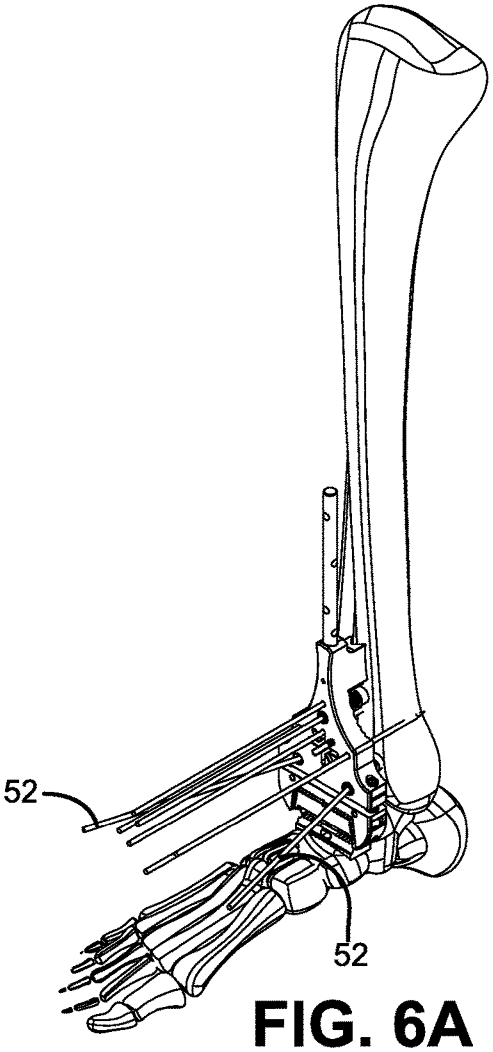
FIG. 6A illustrates a front, side perspective view of the device, bones and fasteners of FIG. 5A and illustrates an exemplary step in using the device.
Figure 6B:
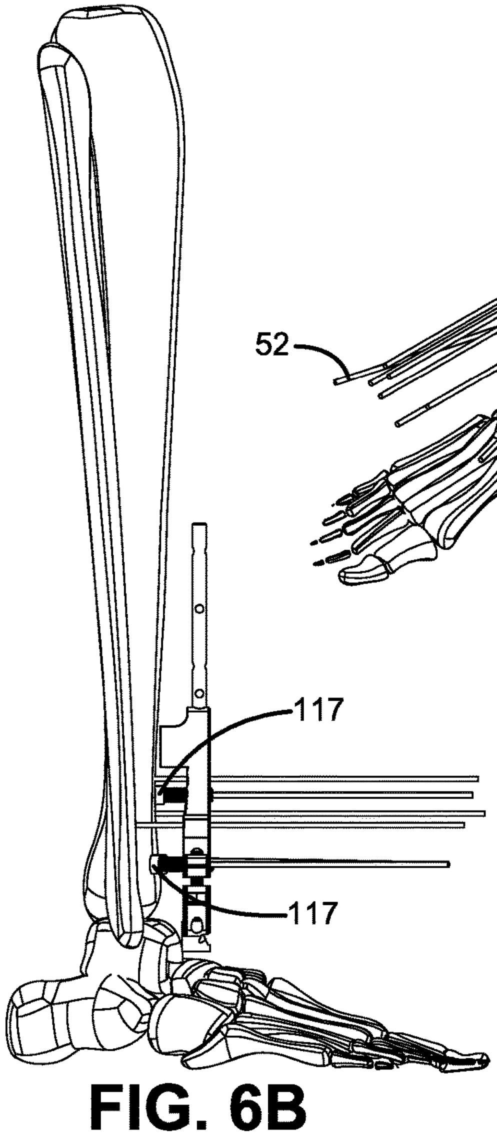
FIG. 6B illustrates a side elevation view of the device, bones, and fasteners of FIG. 6A.
Figure 6C:
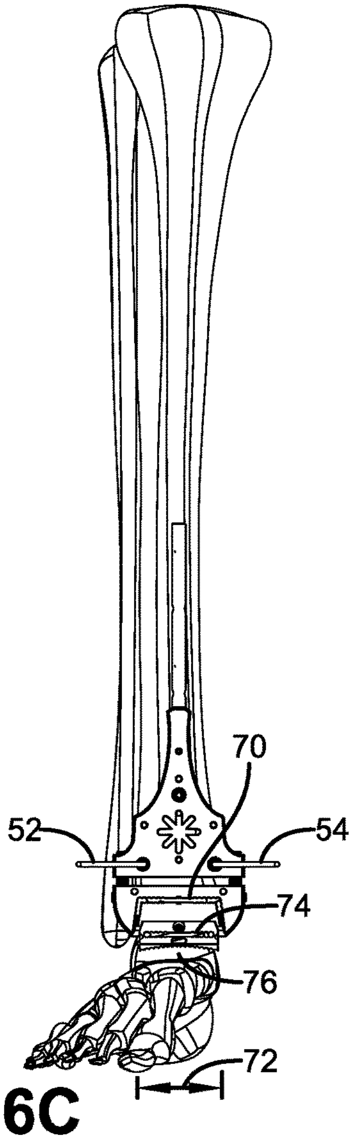
FIG. 6C illustrates a front elevation view of the device, and bones and fasteners of FIG. 6A.
Figure 7A:
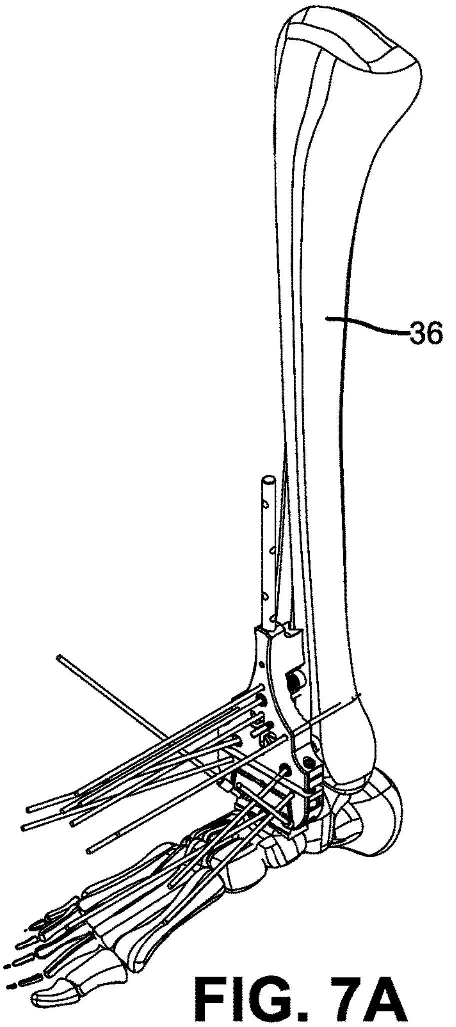
FIG. 7A illustrates a front, side perspective view of the device, bones and fasteners of FIG. 6A and illustrates an exemplary step in using the device.
Figure 7B:
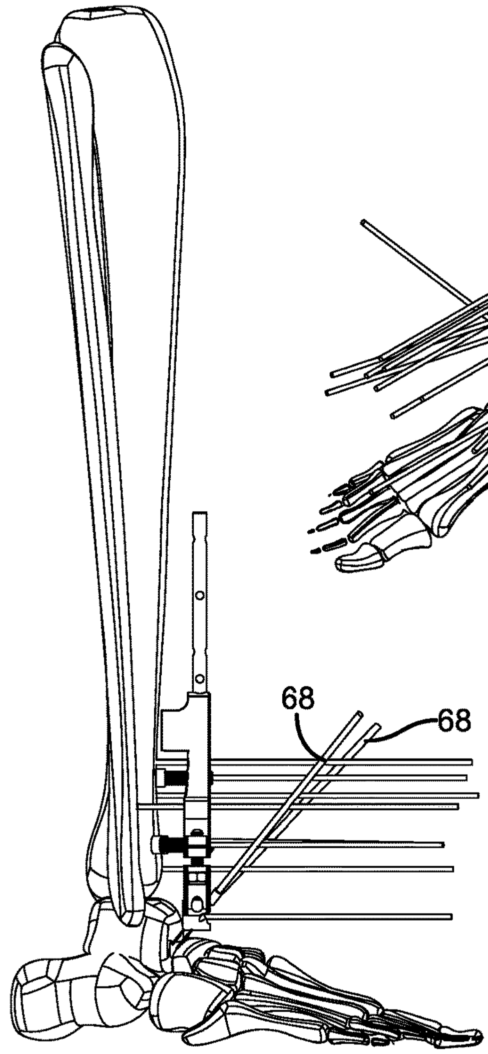
FIG. 7B illustrates a side elevation view of the device, bones, and fasteners of FIG. 7A.
Figure 7C:
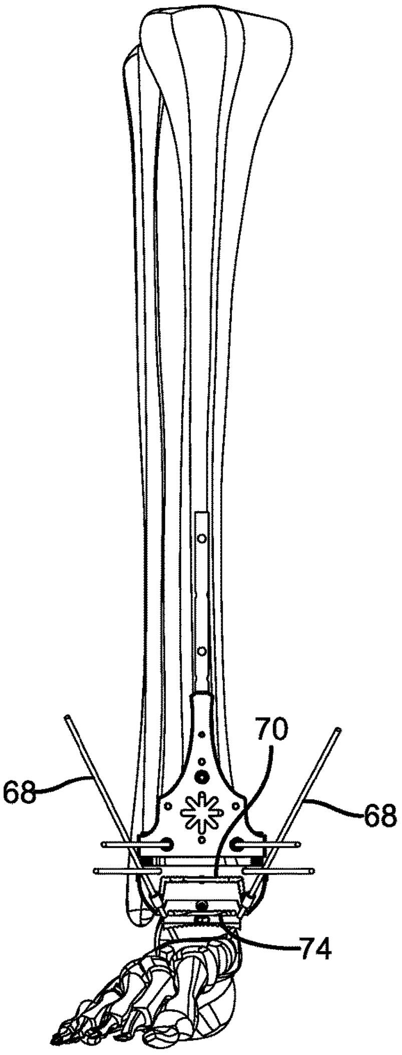
FIG. 7C illustrates a front elevation view of the device, and bones and fasteners of FIG. 7A.
Figure 8A:
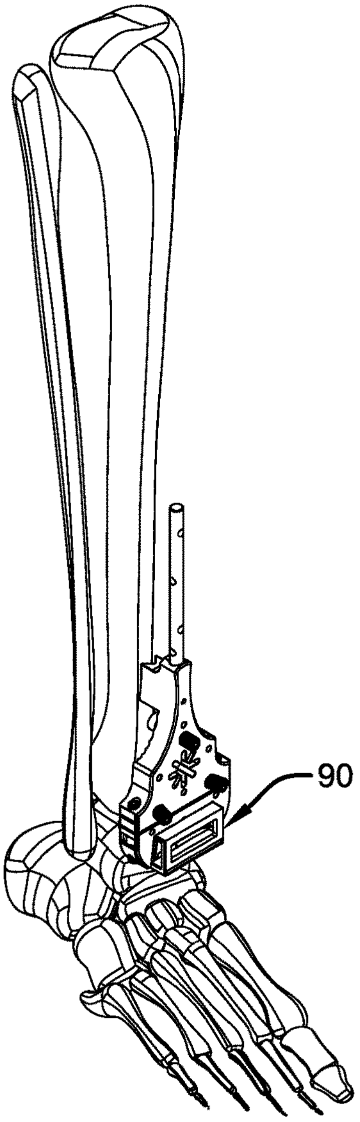
FIG. 8A illustrates a front, side perspective view of a tibial adjustment and cutting device of another embodiment of the present invention placed in front of a human tibia bone and over bones of human foot.
Figure 8B:
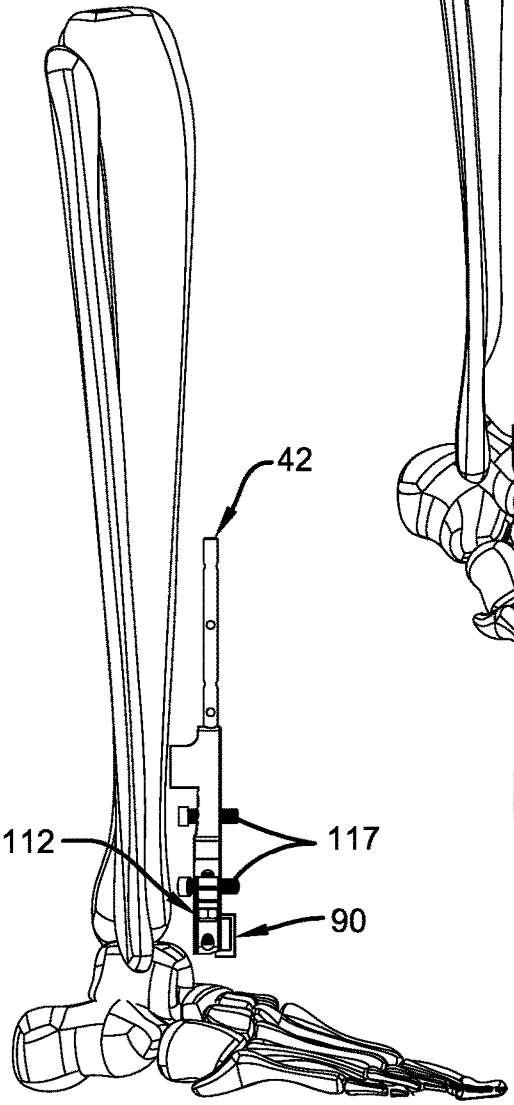
FIG. 8B illustrates a side elevation view of the device and bones of FIG. 8A.
Figure 8C:
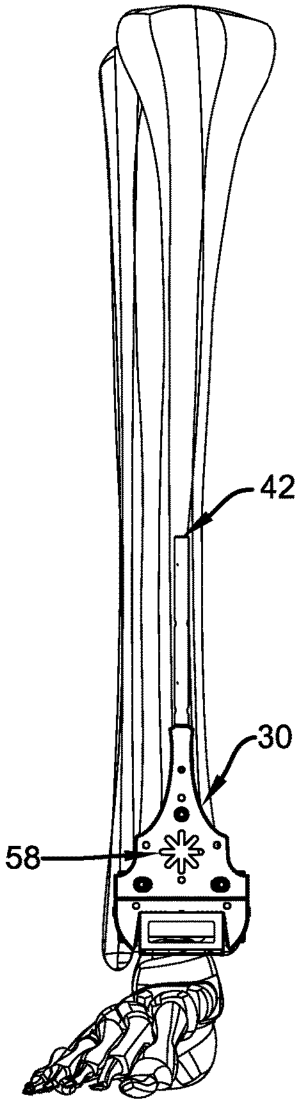
FIG. 8C illustrates a front elevation view of the device and bones of FIG. 8A.

The innovation is now described with reference to the drawings, wherein like reference numerals are used to refer to like elements throughout. In the following description, for purposes of explanation, numerous specific details are set forth to provide a thorough understanding thereof. It may be evident, however, that the innovation can be practiced without these specific details. In other instances, well-known structures and devices are shown in block diagram form to facilitate a description thereof. Various embodiments are discussed hereinafter. It should be noted that the figures are described only to facilitate the description of the embodiments. They are not intended as an exhaustive description of the invention and do not limit the scope of the invention. Additionally, an illustrated embodiment need not have all the aspects or advantages shown. Thus, in other embodiments, any of the features described herein from different embodiments may be combined.

As noted above, there exists a long-felt need in the art for an improved medical device that can be used in a total ankle replacement procedure. More specifically, there exists a long-felt need in the art for a tibial alignment guide and cutting system that is sufficiently modular to account for a plurality of patient conditions during a total ankle replacement procedure. In addition, there exists a long-felt need in the art for a tibial alignment guide and cutting system that can be used with a mini c-arm during a total ankle replacement procedure.

The present invention, in one exemplary embodiment, is comprised of a tibial alignment guide and cutting system 10. Referring initially to the drawings, FIG. 1A illustrates a front, side perspective view of a tibial adjustment and cutting device 10 of one embodiment of the present invention placed in front of a human tibia bone and over bones of human foot. The system 10 is comprised of a device 10. The device 10 is primarily comprised of a device front face 12; a device rear face 14 opposite the front face 12 that may be configured to face a human tibia 36; a device thickness 16 extending from the device front face 12 to the device rear face 14; a device top 18; a device bottom 20 that may be configured to be positioned over a user's foot; a device height 22 extending from the device top 18 to the device bottom 20 and perpendicular to device thickness 16; a device left side 24; a device right side 26; a device width 28 extending from the device left side 24 to the device right side 26 and perpendicular to the device height 22 and device thickness 16; and a lower portion 96 that may include a device body.

The device 10 is preferably sterile. In one embodiment, the device 10 is disposable. Without being bound by any particular theory, the device 10 may allow for a series of micro or macro adjustments in all planes to insure proper resection of bone. Optional sequences and methods of use are shown in the illustrations. It will be understood that the methods and sequences are exemplary. The steps of any method described herein may be performed in any suitable order and steps may be performed simultaneously if needed.

Figure 18A:
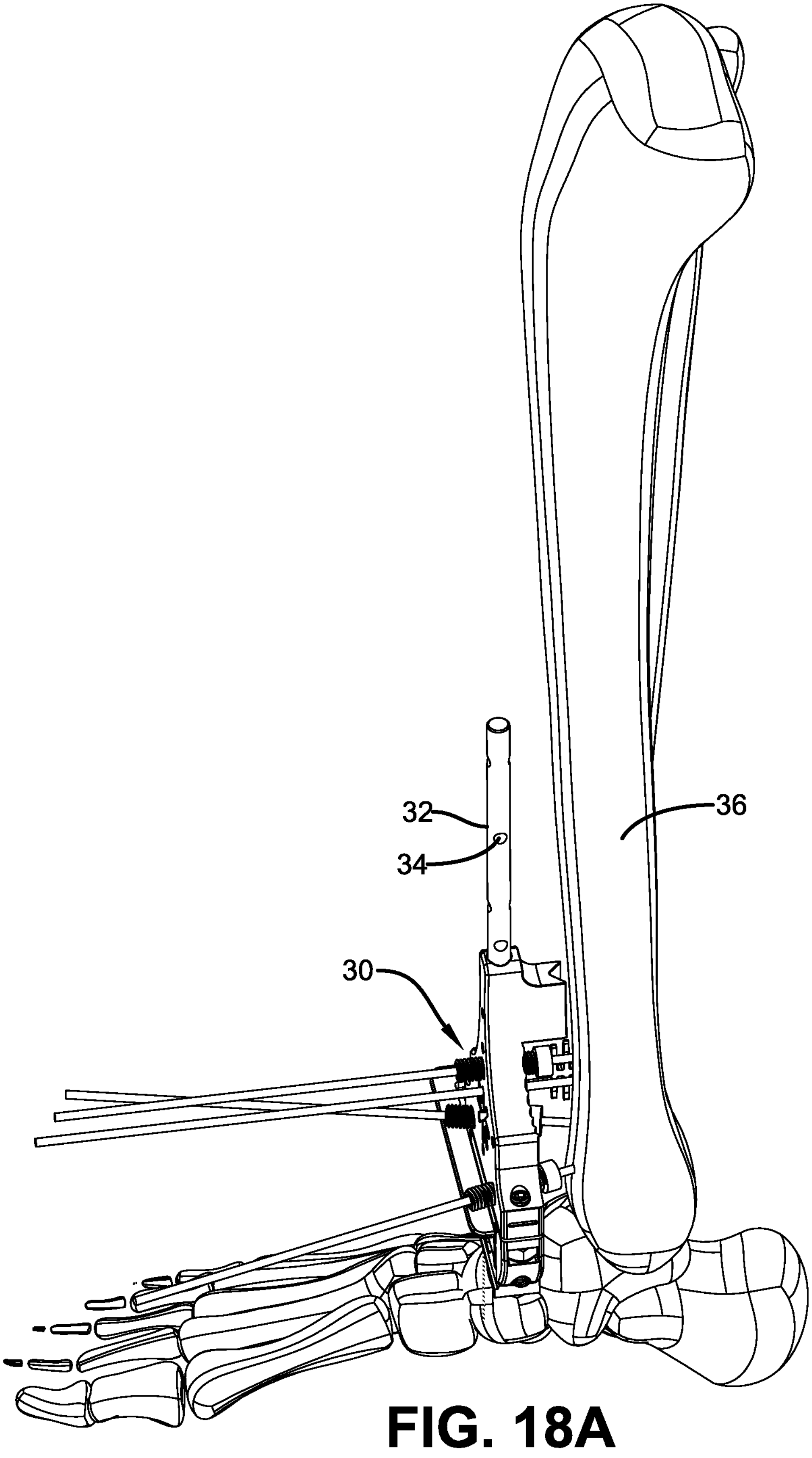
FIGS. 18A-18C illustrate side perspective view of the device and bones of FIG. 1A together with exemplary fasteners, with FIG. 18C showing forward tilting of the device three degrees from a plane perpendicular to the ground.
Figure 18B:
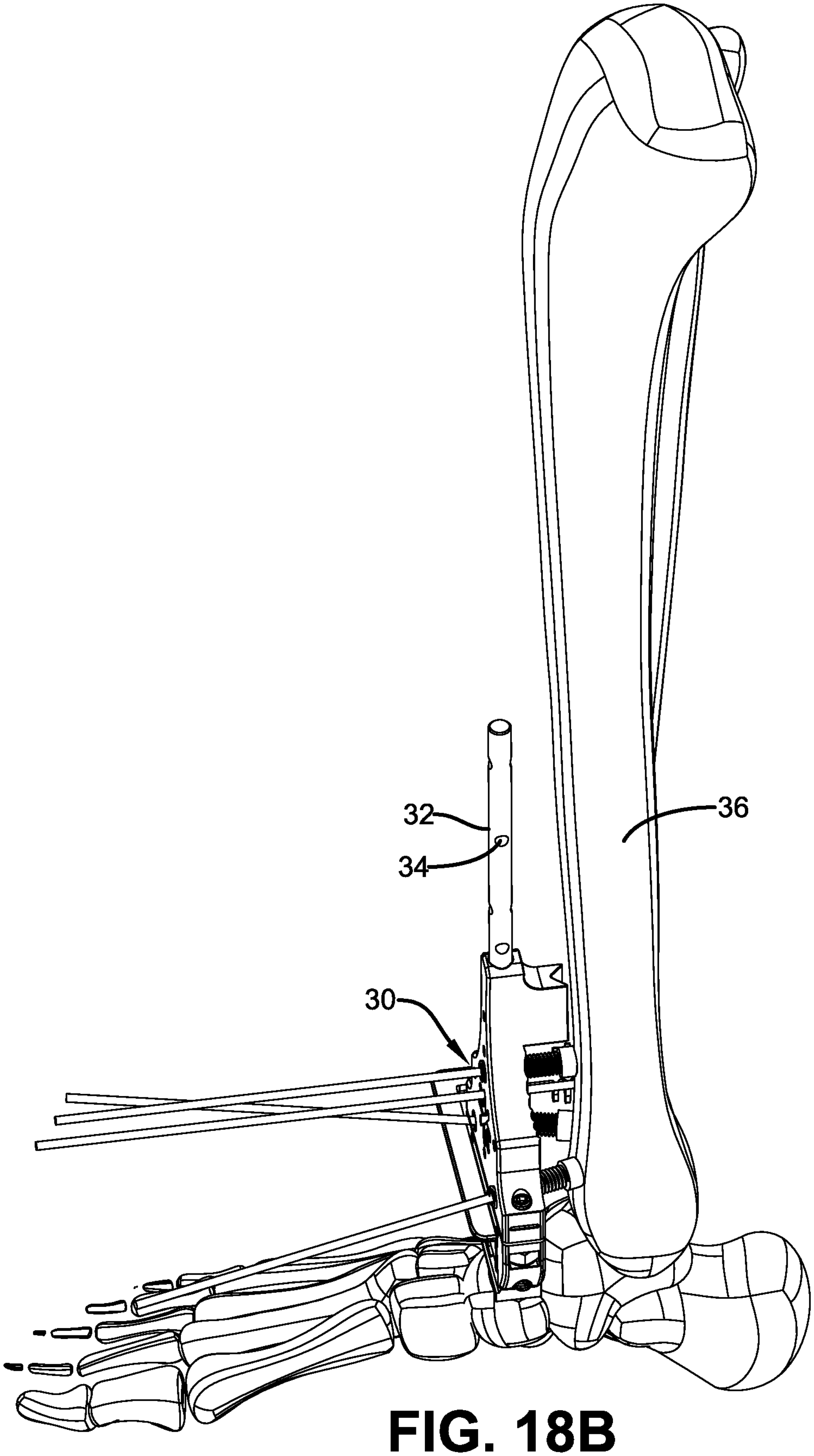
Figure 18C:
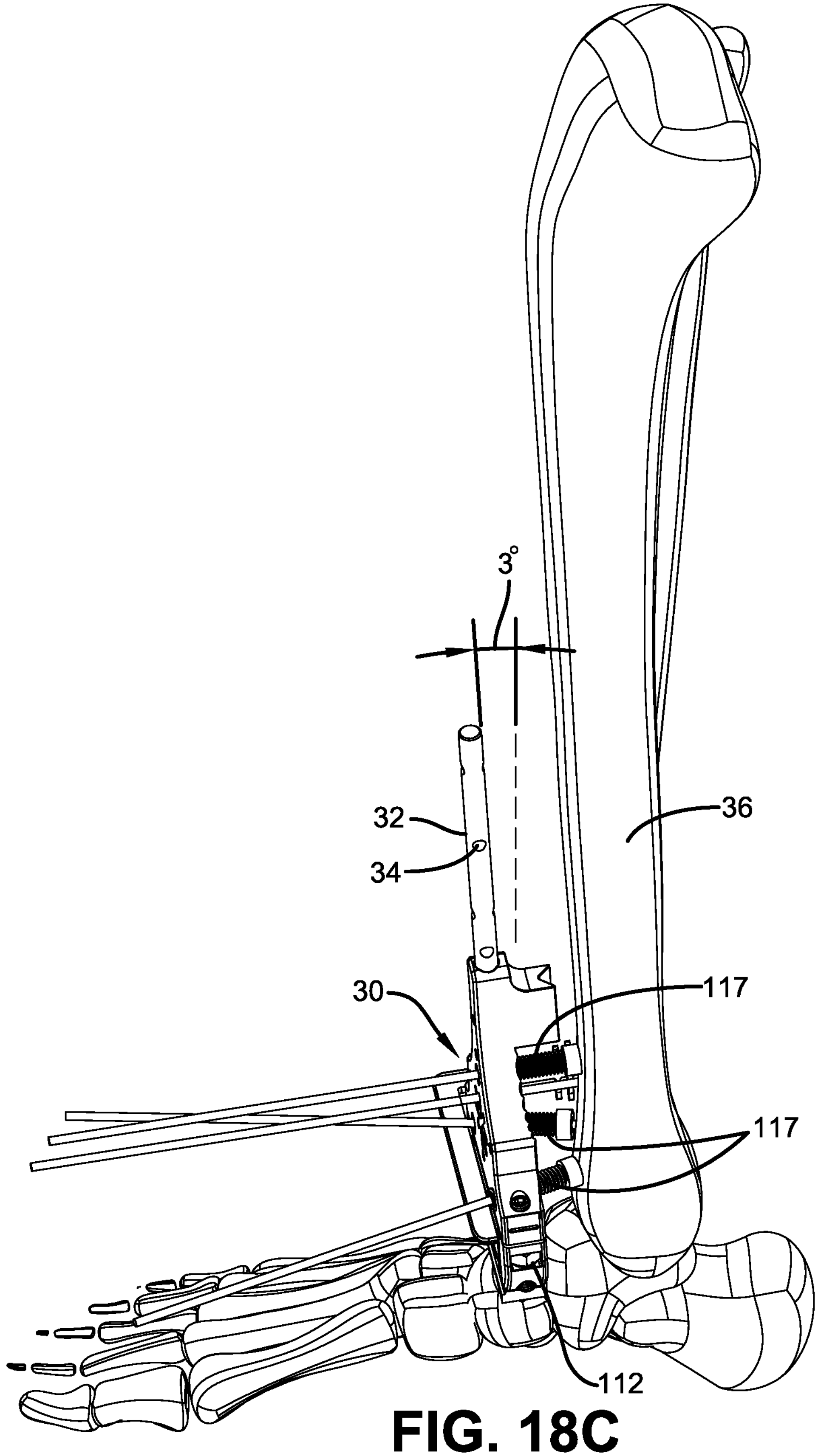
Figure 19A:
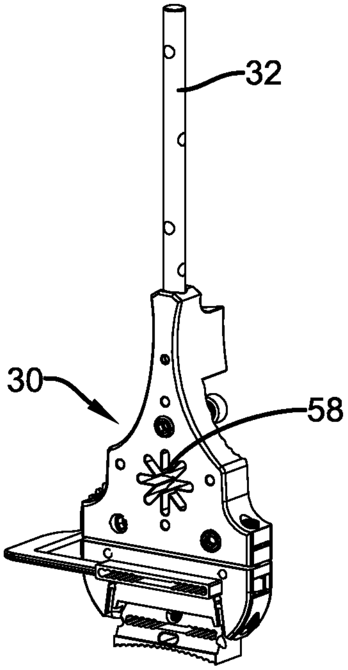
FIGS. 19A-19D illustrates a perspective, exploded views of a tibial adjustment and cutting device of one embodiment of the present invention that includes a slotted angel wing.
Figure 19B:
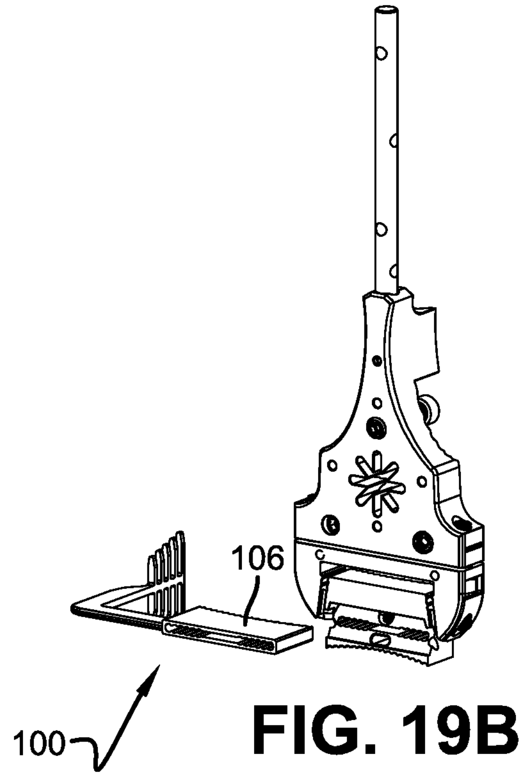
Figure 19C:
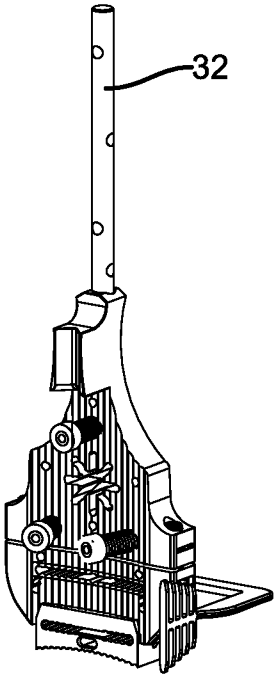
Figure 19D:
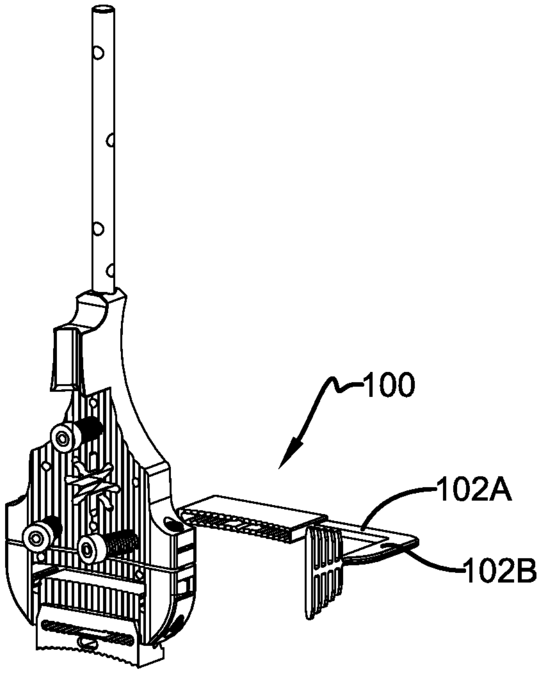

The device 10 may include an upper portion 94 comprising at least one vertical rod 32 extending upwardly from the device body 30 and comprising a plurality of markings. In the illustrated embodiment, the plurality of markings are in the form of a plurality of rod holes 34 that are 90 degrees relative to each other (e.g., at the 12, 3, 6, and 9 o'clock positions) and spaced along the rod height 44. Without being bound by any particular theory, the vertical rod 32 may be radiopaque and the surgeon may irradiate the rod 32 with x-ray and use the positioning of the rod holes 34 to determine proper positioning of the device 10. In use, the device 10 and vertical rod 32, may tilt slightly forwardly, 0-5 degrees (or more) forwardly (e.g., 3 degrees from a plane perpendicular to the ground as shown in FIG. 18C, where the top screw 117 is titling the device 10 more forwardly) or slightly rearwardly/backwardly, e.g., 0-5 degrees backwardly (or more) due to the top screw 117 tilting the device 10 more backward. In other words, the top screw 117 may be used to tilt the device 10 forwardly or backwardly.

The device 10 may include one or more of the following features, either alone, or in any suitable combination.

In addition, the vertical rod 32 may be positioned in front of, for example, the tibia 36. The vertical rod 32 may include a bottom end 40 connected to the device body 30, a free top end 42 forming the top of the device 10, and a height 44 extending from the bottom end 40 to the free top end 42 and parallel to the device height 22. Optionally, the vertical rod 32 may also be affixed to the tibia 36 using at least one fastener through one of the holes 34 in the vertical rod 32.

In some embodiments, the device body may be transparent and/or radiolucent to increase visibility to the surgeon. In the illustrated embodiments, the device body 30 includes at least one perpendicular fastener hole 46 that extends from the front face 12 to the rear face 14 and perpendicular to the device width 28 as well as at least one angled fastener hole 50 that extends from the front face 12 to the rear face 14 at an angle (e.g., 10 to 80 degrees) relative to the device width 28 and inwardly.

In the illustrated embodiment, the device body 30 includes a plurality of perpendicular fastener holes 46 that are positioned in a triangle pattern with a top perpendicular fastener hole 46 located at the triangle apex in the center of the device width 28 and left and right perpendicular fastener holes 46 below the top perpendicular hole 46 that forms the base of the triangle. Each of the perpendicular fastener holes 46 is configured to receive at least one perpendicular fastener 48. Fasteners 48 for use with the present device 10 include, without limitation, fasteners typically used for fixation, including pins, screws or wires, each of which may be smooth, threaded or drill tipped. In some embodiments, the fasteners 48 may be canulated.

In the exemplary embodiments, the device 10 also includes at least one left-angled fastener hole 50 and at least one right-angled fastener hole 50 that are at approximately the same height and receive at least one angled hole fastener 52 such that the rear ends 54 of the angled hole fasteners 52 may converge. In other words, the distance between the angled hole fasteners 52 may decrease rearwardly along the angled hole fasteners 52. Without being bound by any particular theory, the convergence of the rear ends 54 of the angled hole fasteners 52 allows for ease of proper positioning of the device 10. The angled hole fasteners 52 are preferably straight but so-named merely to differentiate from the other fasteners described herein.

Figures 21A, 21B:
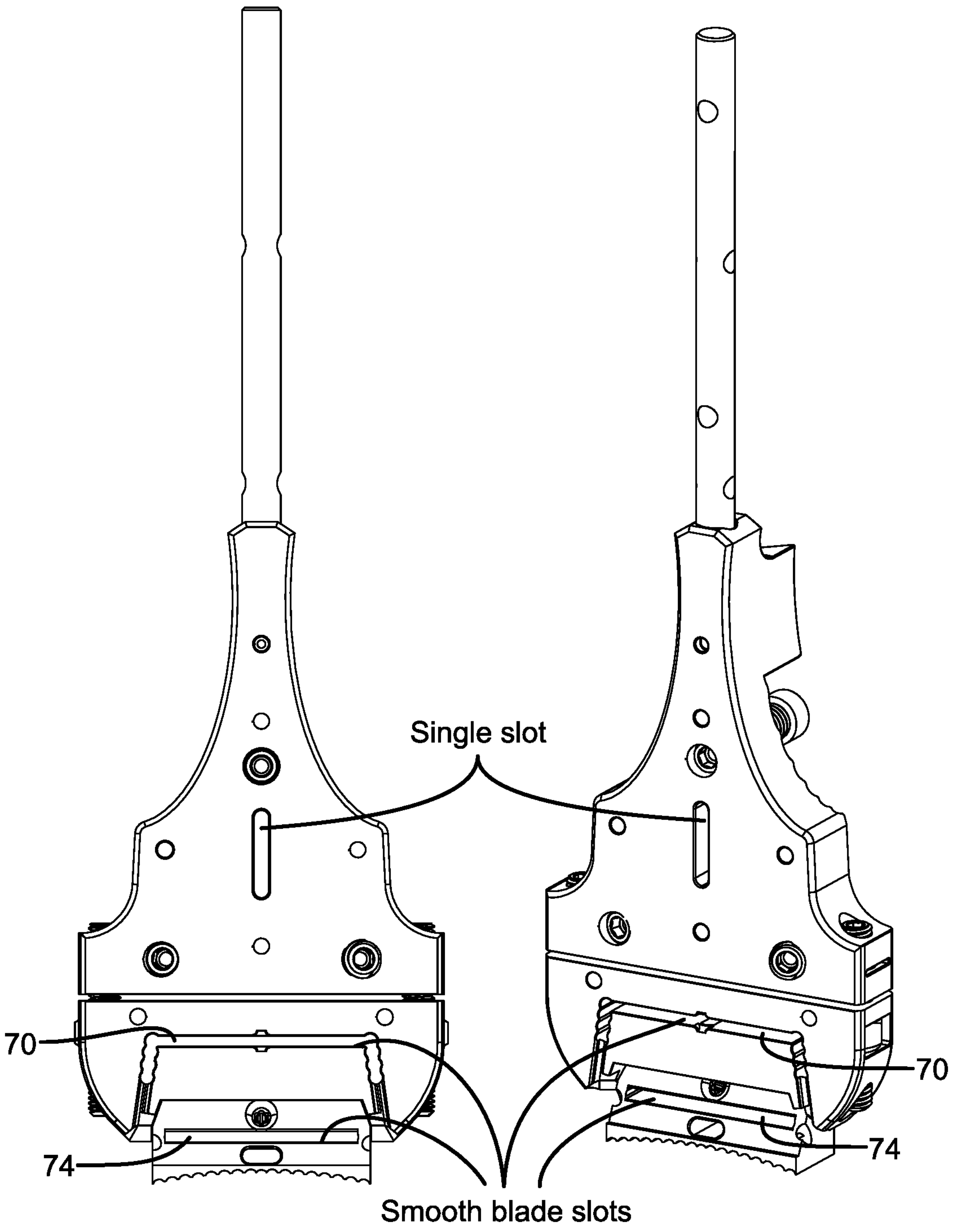
FIGS. 21A and 21B illustrate a front elevation, exploded view and a perspective exploded view of a tibial adjustment and cutting device of one embodiment of the present invention that includes single slot instead of a star cut-out as well as smooth tibial and talar cutting slots.
Figure 22A:
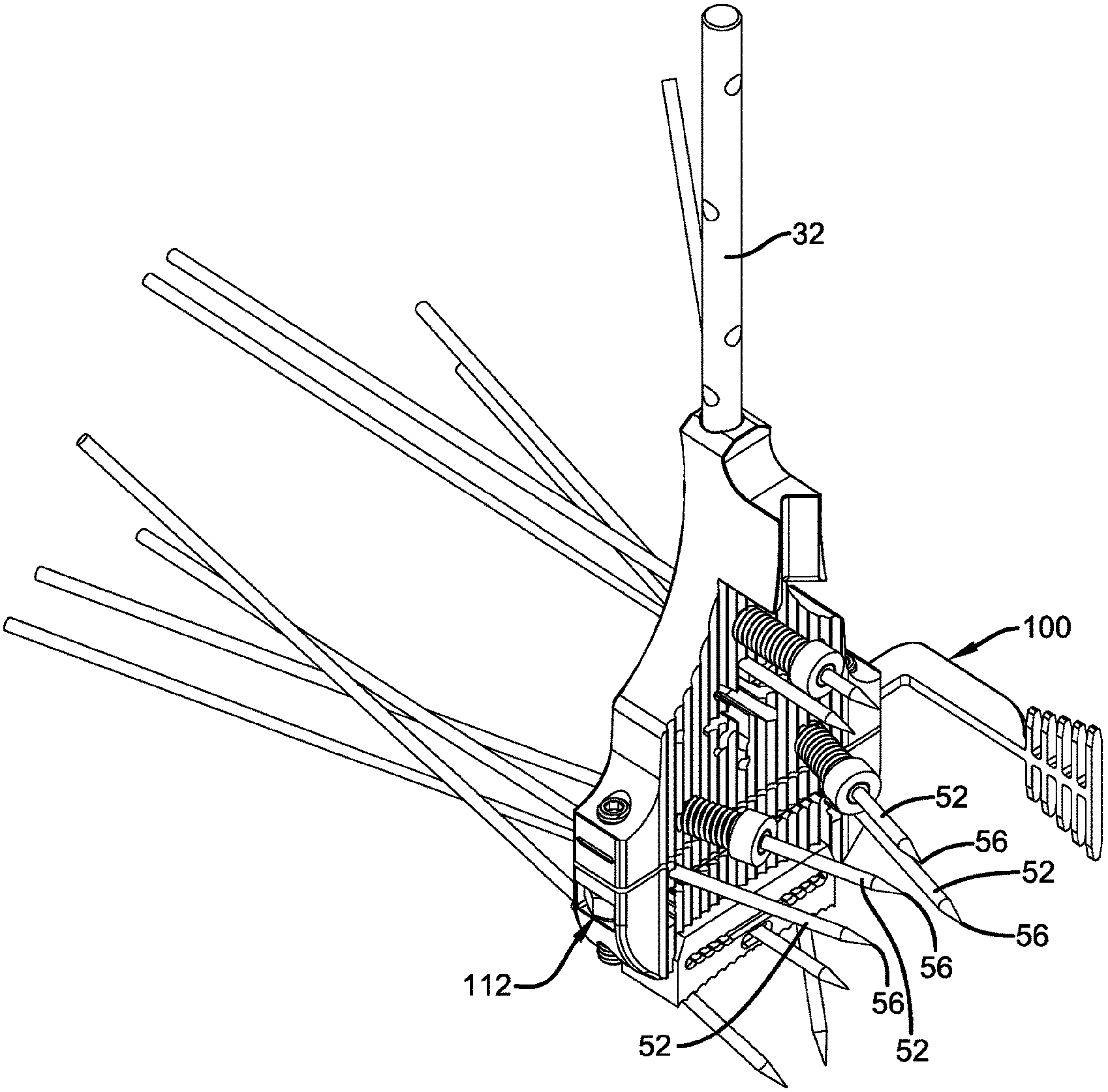
FIGS. 22A-22C illustrate a side perspective view, top plan view and bottom plan view of the device of FIG. 1A together with exemplary fasteners.
Figure 22B:
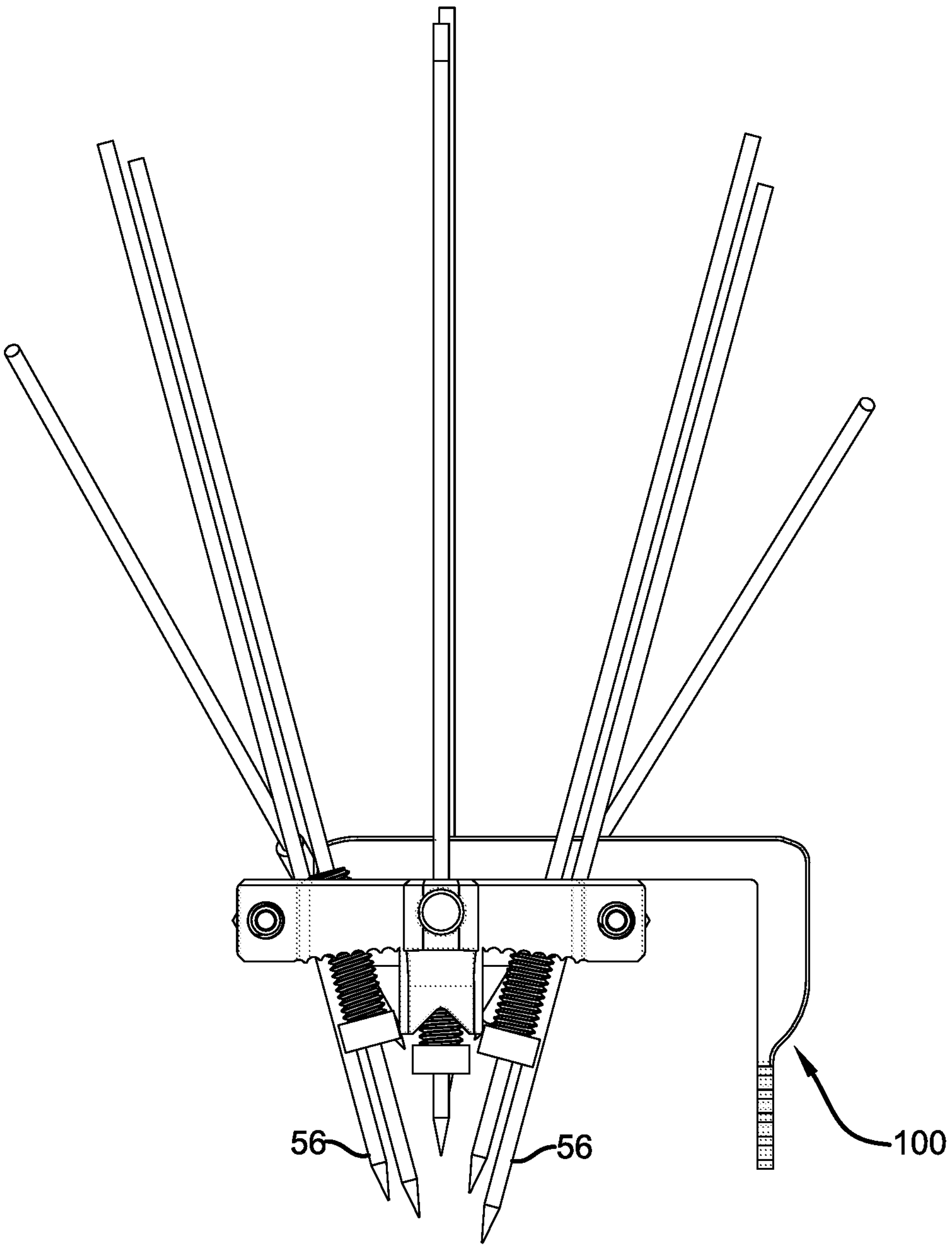
Figure 22C:
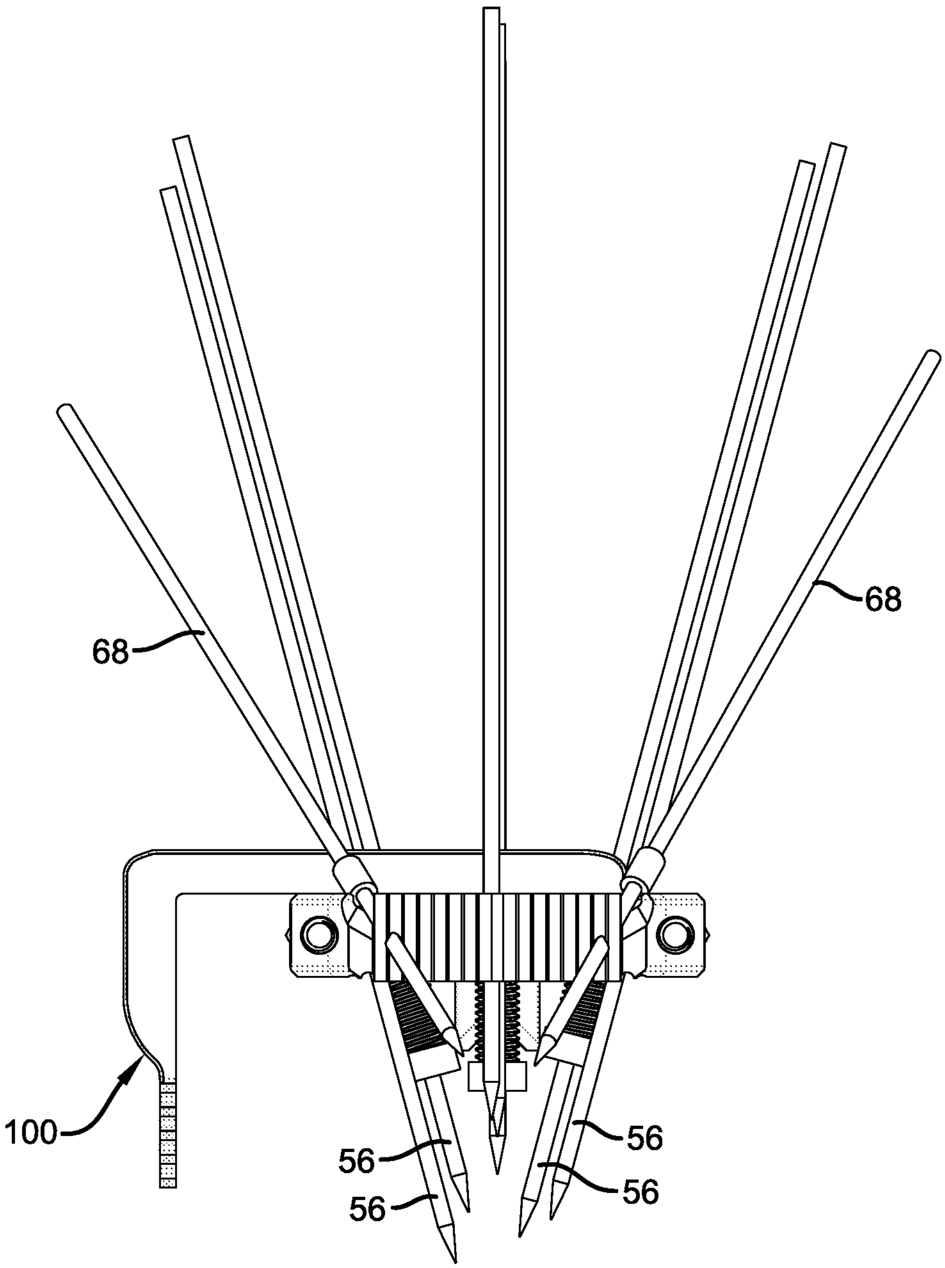
Figure 23A:
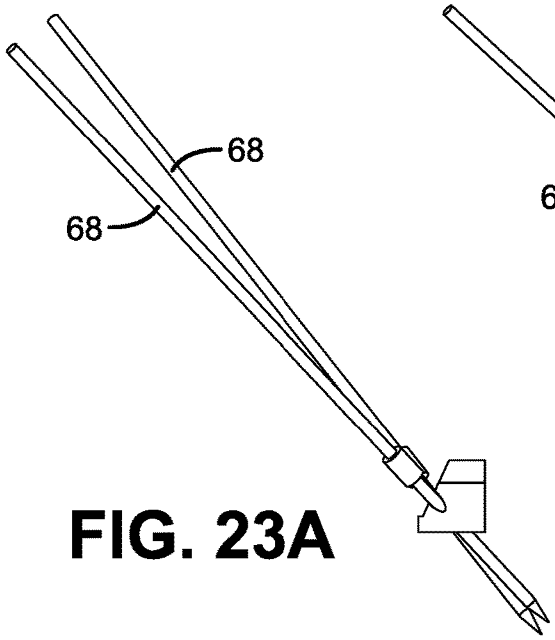
FIGS. 23A-23C illustrates elevation and perspective views of a removable talar cutting piece of one embodiment of the present invention together with exemplary fasteners.
Figure 23B:
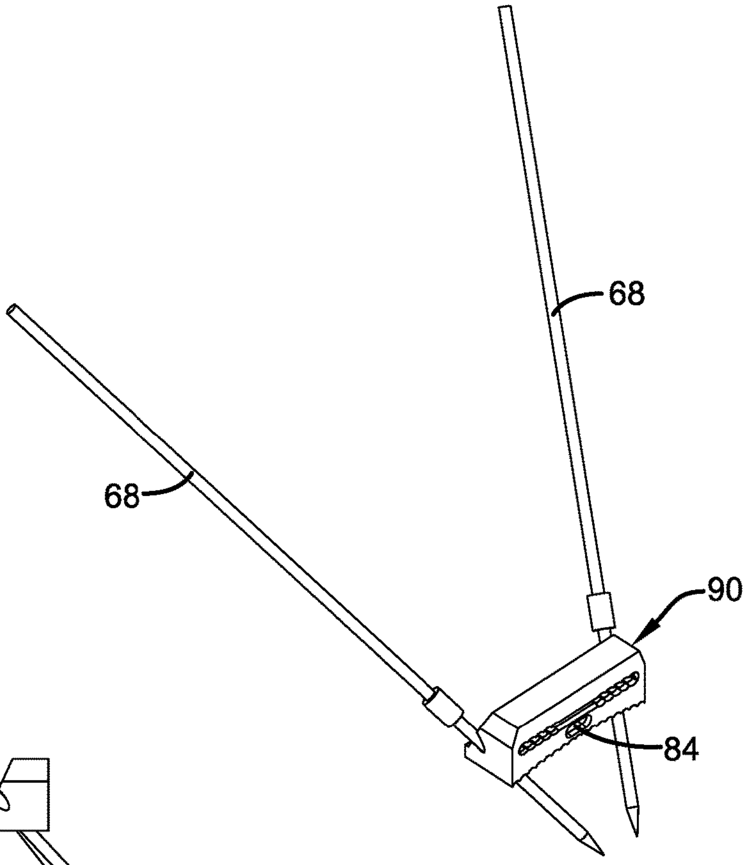
Figure 23C:
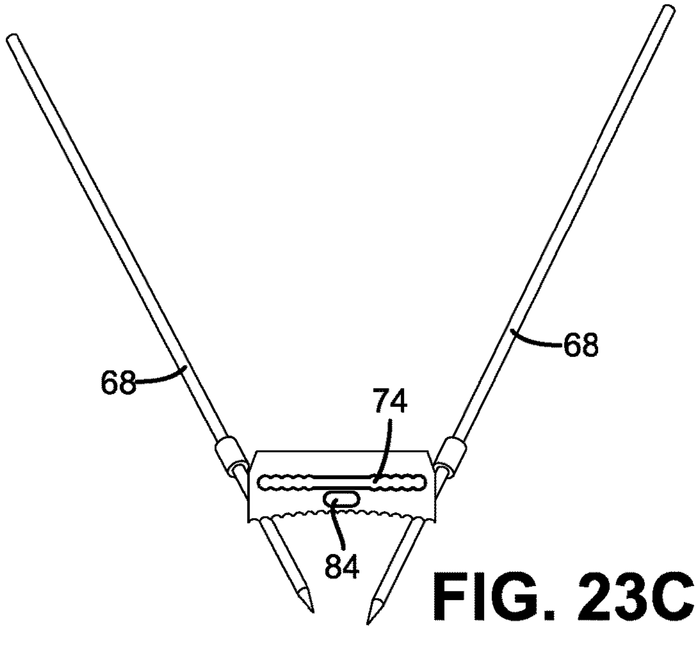

The device body 30 may further include at least one star-shaped cut-out 58 extending from the front face 12 to the rear face 14 and located approximately in the center of the width 28. The star-shaped cut-out 58 may include a center 60 and at least one angled slot 62 radiating from the center 60 and preferably spaced at regular intervals. At least one cut-out fastener 64 may be placed in one or more of the angled slots 62. Without being bound by any particular theory, the star-shaped cut-out 58 may allow for a "joystick" positioning pin. In one embodiment, the star-shaped cut-out 58 may be in the form of a single elongated slot (as shown in FIGS. 21A-21B), and a pin, k-wire, or other fastener 64 may be inserted through the single elongated slot for stabilization.

The left side 24 and right side 26 of the device body adjacent (i.e., at or near) the device bottom 20 may also include at least one upwardly angled fastener holes 110 that accommodate at least one upwardly angled fasteners 112. Without being bound by any particular theory, the left and right upwardly angled fasteners 112 may allow for the ability to translate inferior to superior to adjust for proper height. This feature may have a "clock dial" marking aspect that allows the user to visually insure both left and right upwardly angled fasteners 112 are at the same distance and parallel. In addition, the device body 30 may include at least one lower angled fastener holes 66 adjacent (i.e., at or near) the device bottom 20 that receive at least one lower angled fastener 68, which extends through device bottom 20 and may be positioned into a bone of the user's foot.

Figure 20:
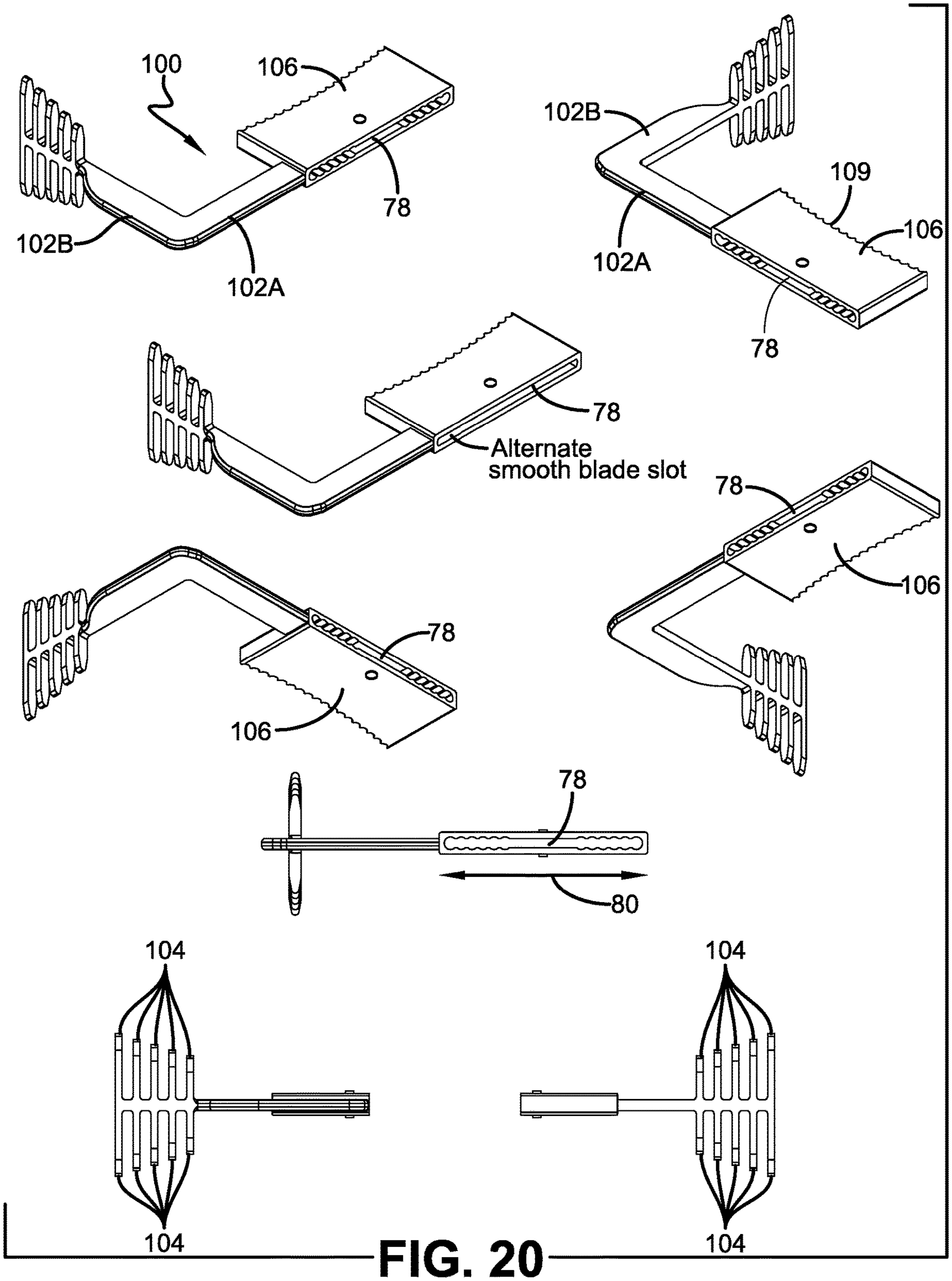
FIG. 20 illustrates various perspective views of a slotted angel wing with one of the angel wings including a smooth (non-toothed) slot.

The device bottom 20 may be positioned, for example, over a user's foot. The device 10 may include one or several cutting slots that are configured to receive a saw blade and permit cutting of bone through the cutting slots. For example, the device body may have at least one tibial cutting slot 70 that may extend the front face 12 to the rear face 14 and may include a tibial cutting slot width 72 parallel to the device body width 28 and may be configured to receive a blade of a saw so that the tibia of the patient's foot may be cut through the device 10. In the embodiment of FIG. 1A, the tibial cutting slot 70 is covered by the angel wing 100, which requires removal of the angel wing 100 before cutting. Alternatively, as shown in FIG. 20 and described below, the angel wing 100 may include at least one angel wing cutting slot 78 that allows use of the saw through the wing 100.

In addition, the device 10 may also include at least one talar cutting slot 74 positioned below the tibial cutting slot 70 that may extend from the front face 12 to the rear face 14 and that may include a talar cutting slot width 76 parallel to the device body width 28 and that may be configured to receive a blade of a saw so that the talus 38 of the patient's foot may be cut through the device 10. The tibial cutting slot 70 and/or the talus cutting slot 74 may be generally rectangular in shape and may include a flat central portion. The slots 70,74 may be smooth (as shown in FIG. 20) or may be toothed. Without being bound by any particular theory, the teeth may be sized to hold one or more fasteners that can be positioned through the cutting slot. Alternatively, as shown in one embodiment of FIG. 20, the cutting slots may be smooth (without teeth). The device body may also include at least one oblong slot 84 having an oblong slot thickness extending from the front face 12 to the rear face 14 and positioned below the talar cutting slot 74. At least one oblong slot fastener 85 may be positioned through the oblong slot 84.

The device bottom 20 may be textured in one embodiment to prevent gross movement on the patient. For example, the device bottom 20 may also include at least one arc-shaped recess 86 at the device bottom 20 that may include at least one tooth 88. In an optional embodiment, the talar cutting slot 74, oblong slot 84, and the arc-shaped recess 86 are part of a removable talar cutting piece 90 that is press fit into, and removable from, the remainder of the device body 30. In uncoupled osteotomies, the removable talar cutting piece 90 may be used without the remainder of the device body 30, and may be held by placing a stem of a handled instrument in at least one recess or hole 92 of the removable talar cutting piece 90.

Figure 9A:
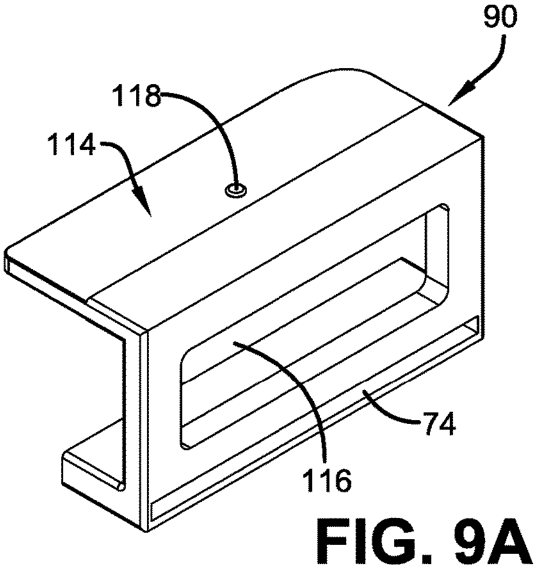
FIGS. 9A-9F illustrate various elevation and perspective views of the removable talar cutting piece of the device of FIG. 8A.
Figure 9B:
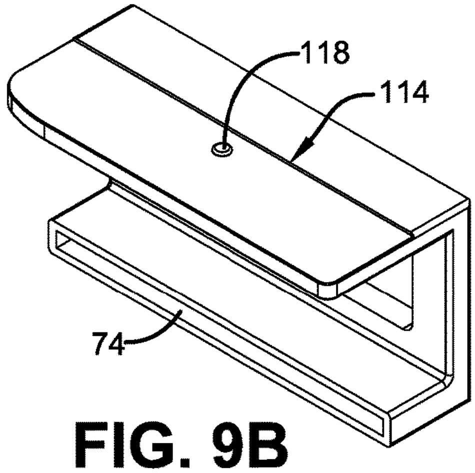
Figure 9C:
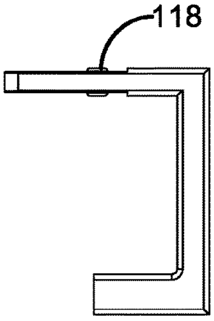
Figure 9D:
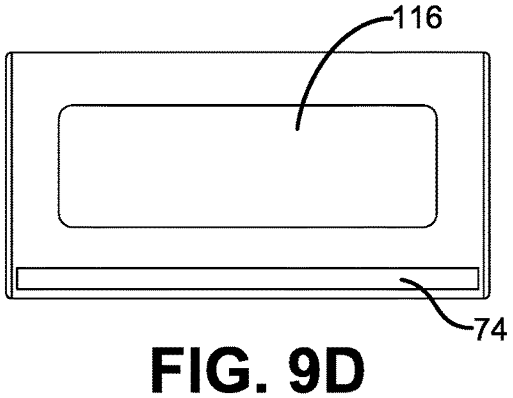
Figure 9E:
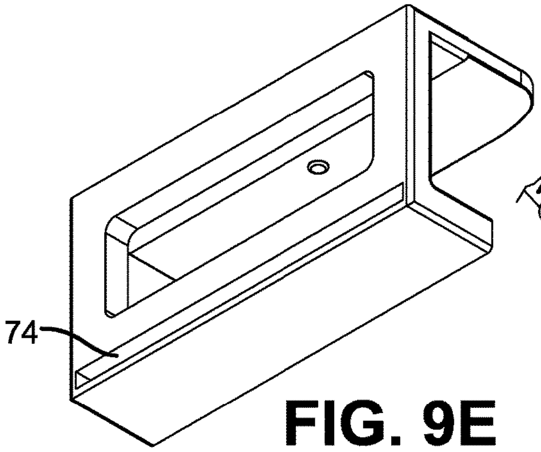
Figure 9F:
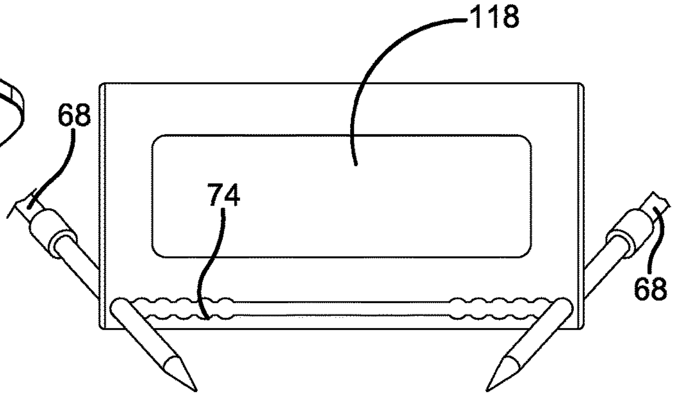
Figure 10A:
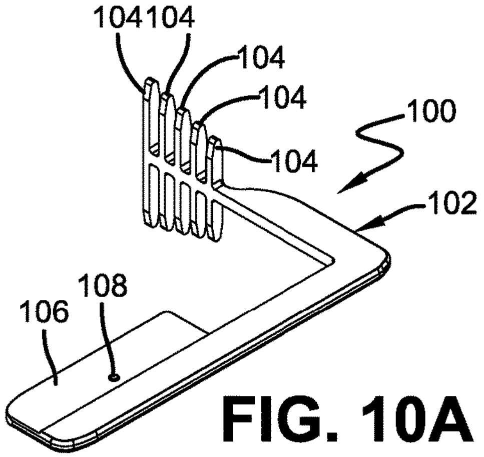
FIGS. 10A-10E illustrate various elevation and perspective views of an angel wing of the device of FIG. 1A.
Figure 10B:
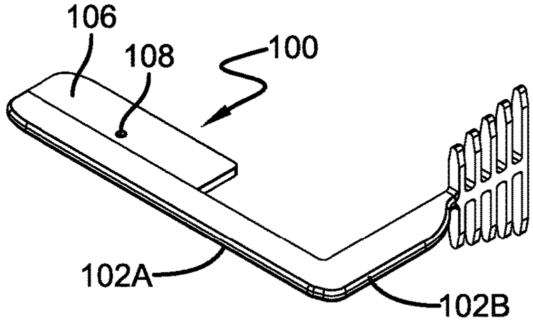
Figure 10C:
Figure 10D:
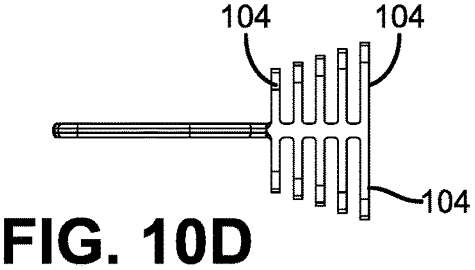
Figure 10E:
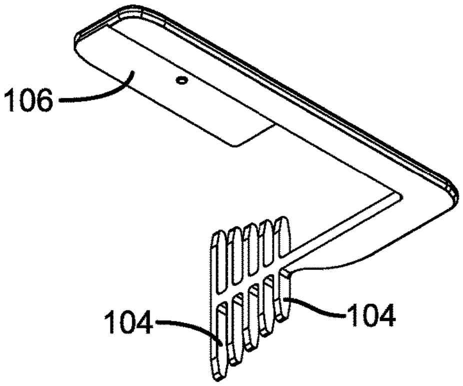

An alternate embodiment of the removable talar cutting piece 90 is shown in FIGS. 8A-8C and 9A-9F. The removable talar cutting piece 90 in this embodiment includes at least one talar cutting slot 74, and optionally at least one window/cut-out 116 and a rearwardly-extending tab 114 that fits into the tibial cutting slot 70. The tab 114 may also include at least one bump 118 to facilitate press fitting into the tibial cutting slot 70. As shown in FIGS. 9A-9F, the tab 114 may be located above and may extend further rearwardly as compared to the talar cutting slot 74. The tibial and talar cutting slots may be smooth or may be toothed. Without being bound by any particular theory, the teeth may be sized to hold one or more fasteners 68 that can be positioned through the cutting slot as shown in FIG. 9F. Alternatively, as shown in one embodiment of FIGS. 9A-9E, the cutting slots may be smooth (without teeth). The device body 30 may be generally triangular in shape as shown in the illustrated embodiment. However, other shapes are possible.

In some embodiments, the device body 30 includes a body upper portion 94 and a body lower portion (referred to herein as a moveable carriage 96) that is positioned below the device body upper portion 94. The device body upper portion 94 and the moveable carriage 96 may be connected by at least one vertically-oriented left-threaded bolt 98 and at least one vertically-oriented right-threaded bolt 99. Optionally, clockwise and counterclockwise adjustment of the heads of the vertically-oriented bolts 98,99 may cause the left side and the right side of the moveable carriage 96 to move toward and away from the device body upper portion 94 as shown in FIGS. 16A-16C and 17A-17B such that the height of the moveable carriage 96 may be adjusted and the moveable carriage 96 may optionally be in a tilted state. The moveable carriage 96 may include a plurality of the aforementioned fastener holes mentioned supra.

Figure 11A:
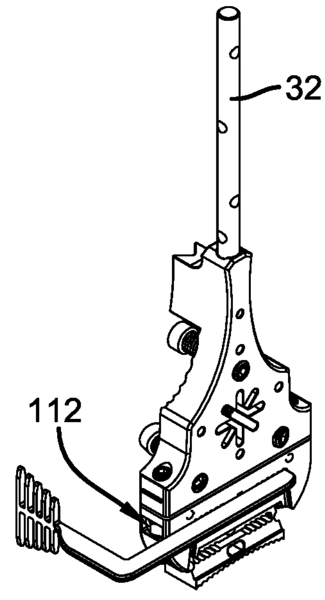
FIGS. 11A-11E illustrate various elevation and perspective views of the device of FIG. 1A, with FIG. 11C showing how the angel wing may be moved to the other side of the device.
Figure 11B:
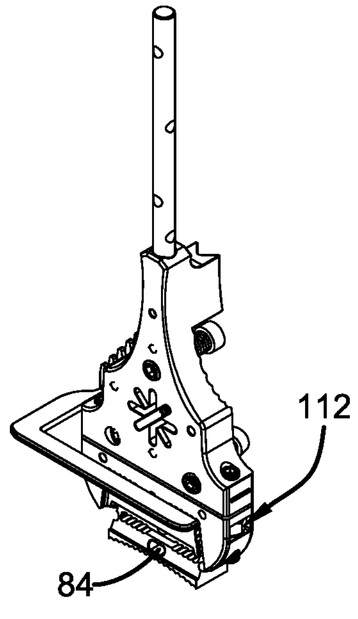
Figure 11C:
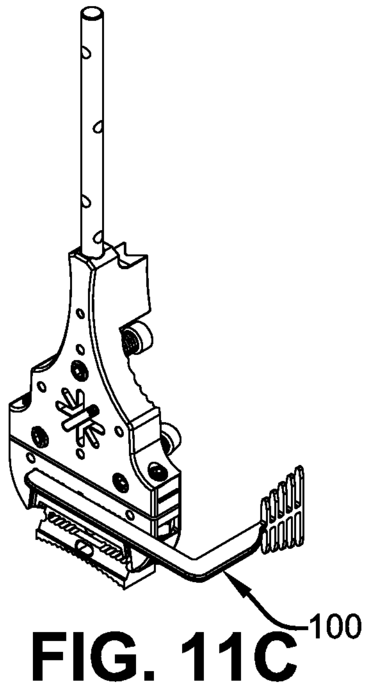
Figure 11D:
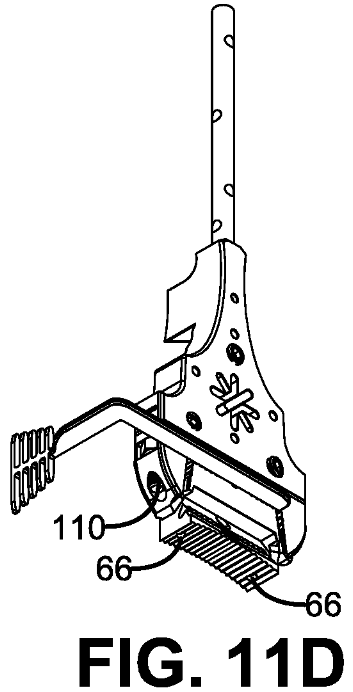
Figure 11E:
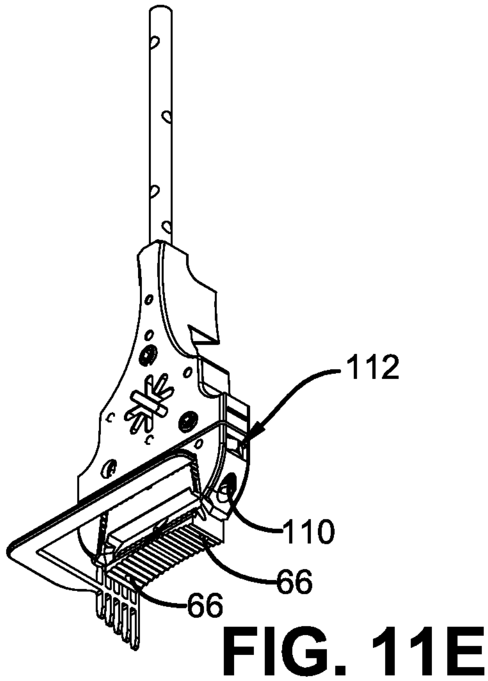
Figure 12A:
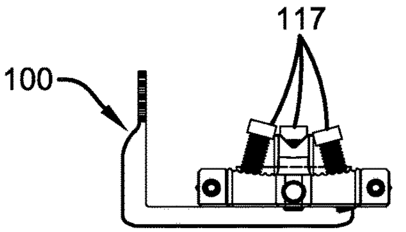
FIGS. 12A-12F illustrate various elevation and plans views of the device of FIGS. 1A and 11A.
Figures 12B, 12C, 12D, 12E:
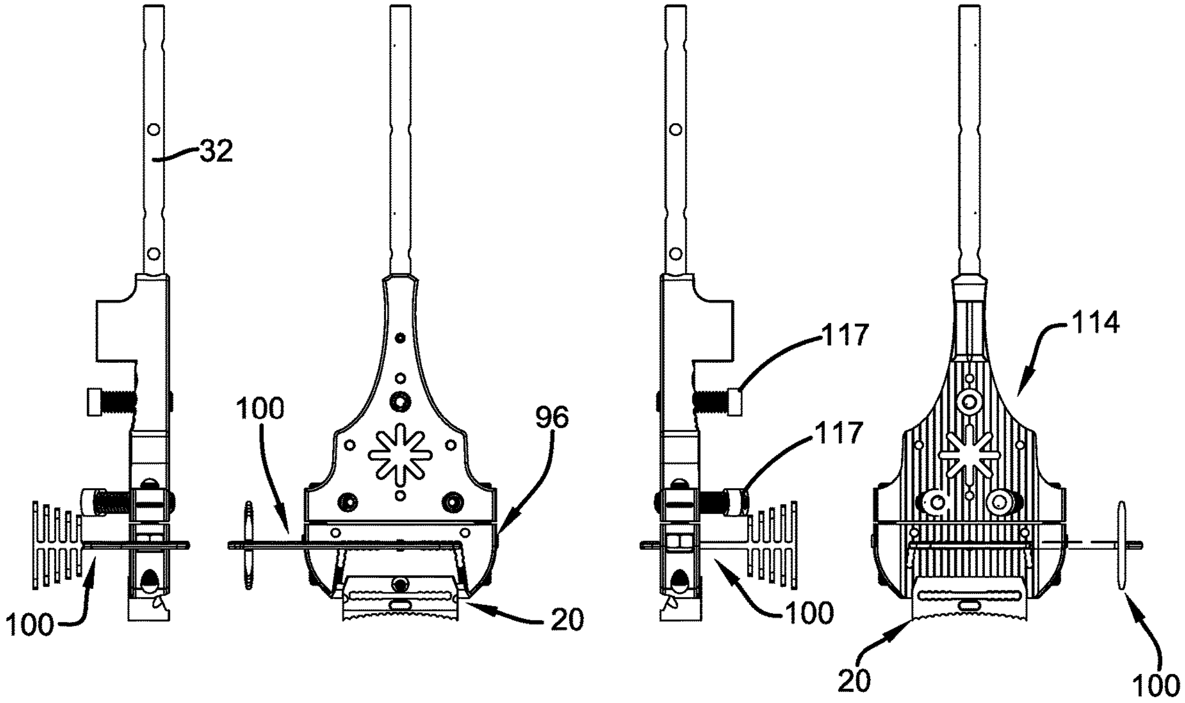
Figure 12F:
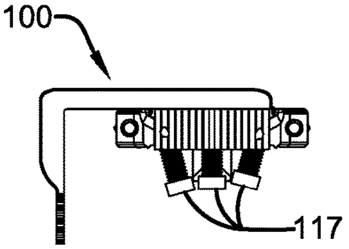
Figure 13A:
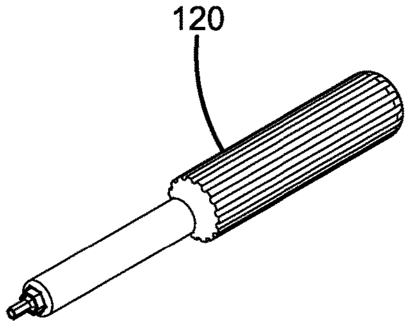
FIGS. 13A-13F illustrate perspective views of various tools and fasteners that may be used with the device of FIG. 1.
Figure 13B:
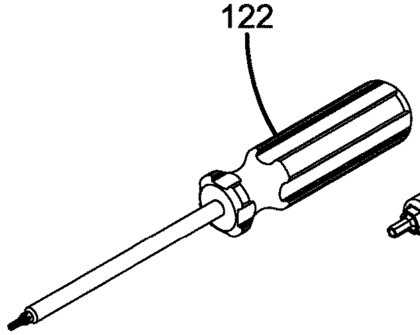
Figure 13C:
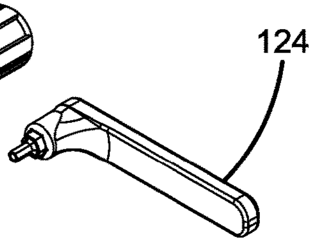
Figure 13D:
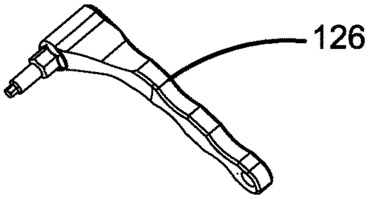
Figure 13E:
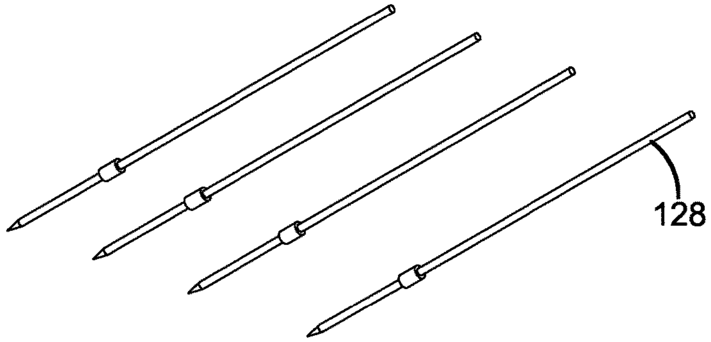
Figure 13F:
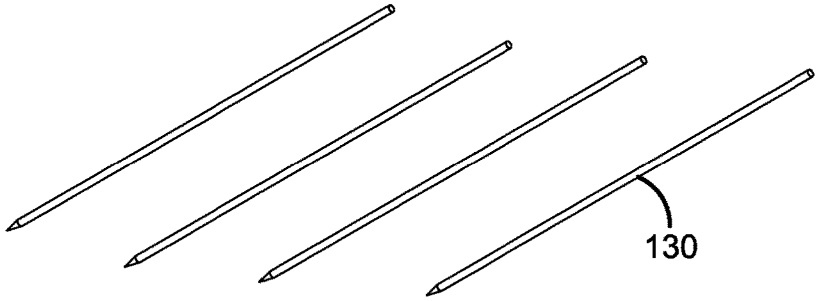
Figure 14A:
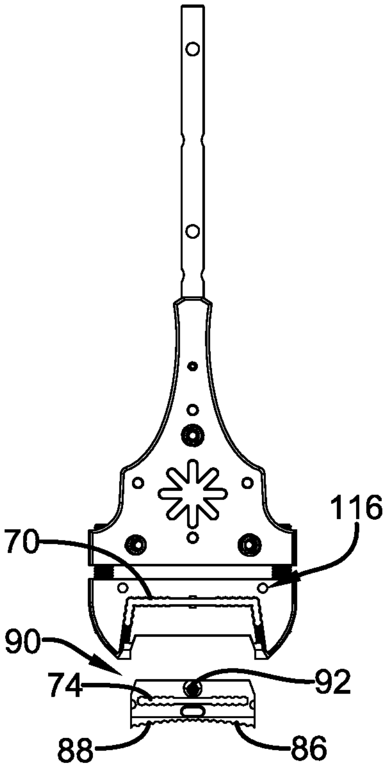
FIGS. 14A-14E illustrate various elevation and perspective exploded views of the device of FIG. 1A and showing how the talar cutting slot, oblong slot and lower angled fastener holes may be located on a removable talar cutting piece.
Figure 14B:
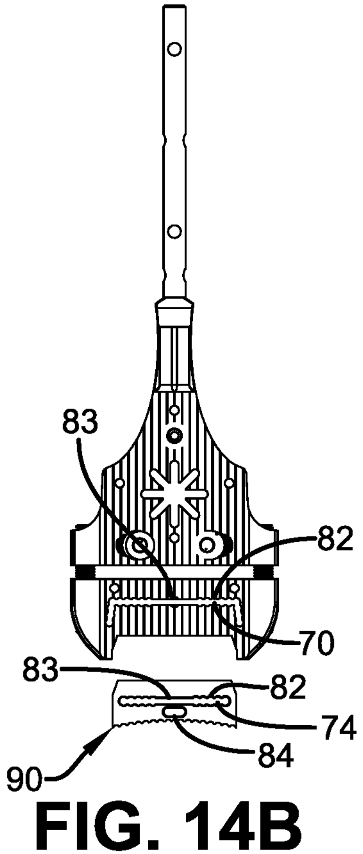
Figure 14C:
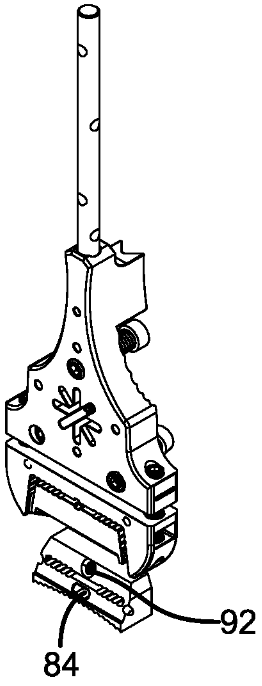
Figure 14D:
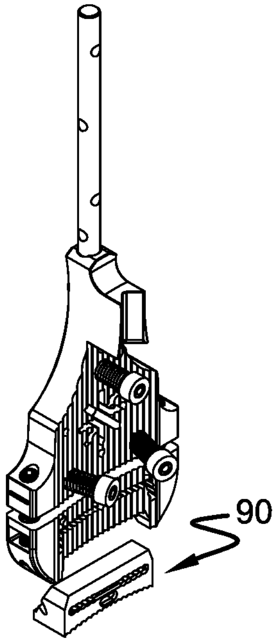
Figure 14E:
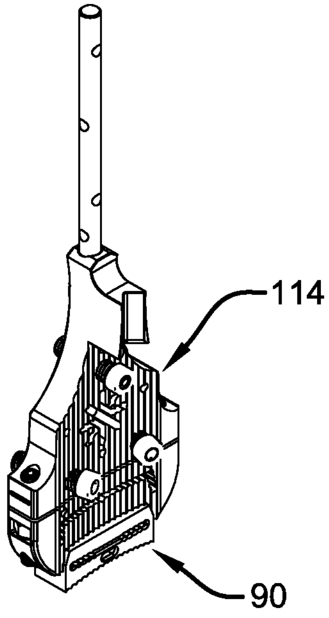
Figure 15A:
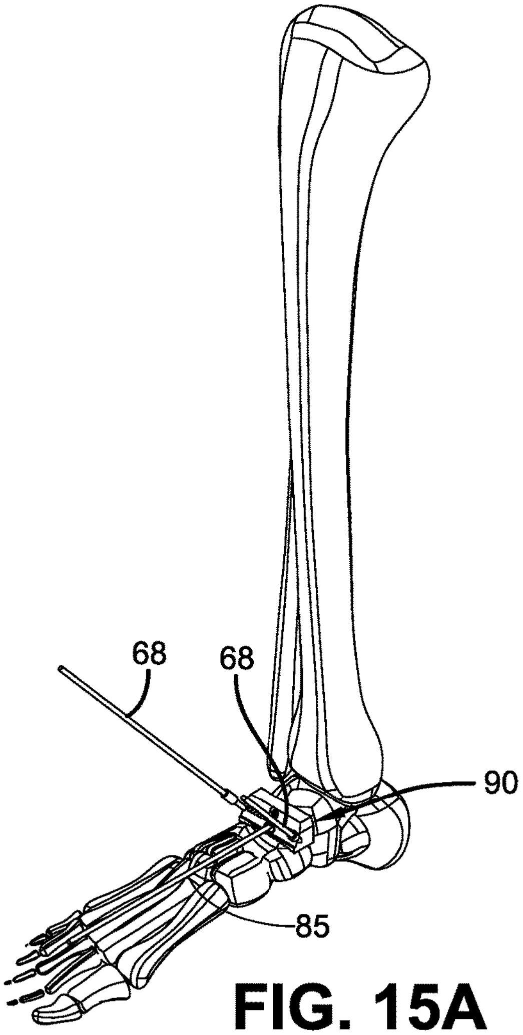
FIG. 15A illustrates a side perspective view of the removable talar cutting piece of FIG. 14A with a fastener placed through the oblong slot and into a bone of the user's foot and lower angled fasteners placed through the lower angled fastener holes and into a bone of the user's foot.
Figure 15B:
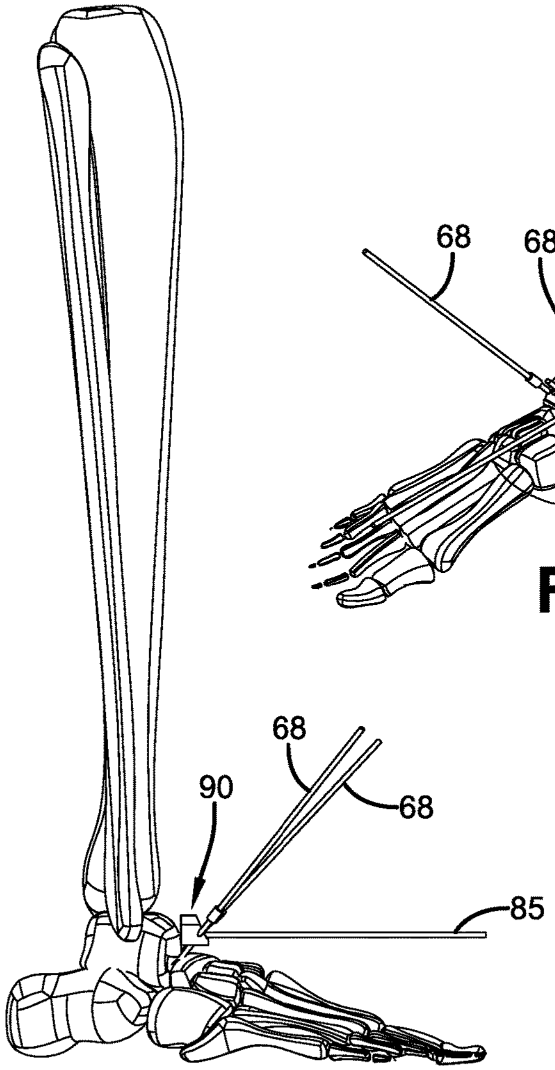
FIG. 15B illustrates a side elevation view of the removable talar cutting piece, bones, and fasteners of FIG. 15A.
Figure 15C:
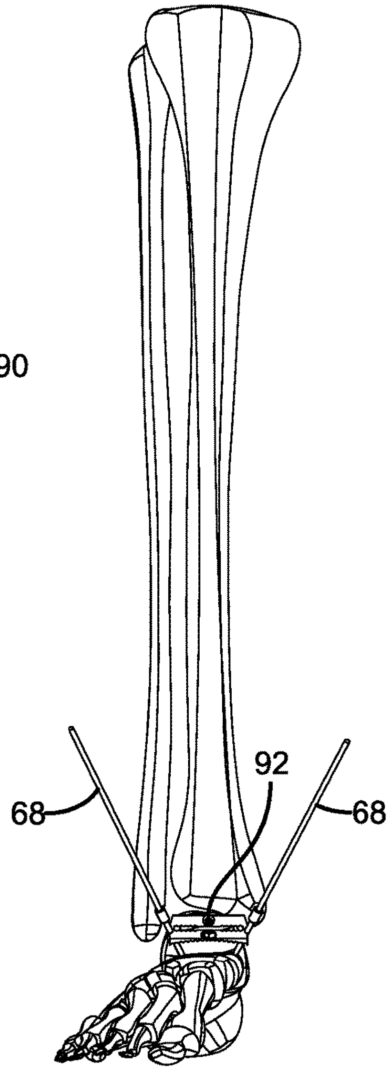
FIG. 15C illustrates a front elevation view of the removable talar cutting piece, and bones and fasteners of FIG. 15A.
Figure 16A:
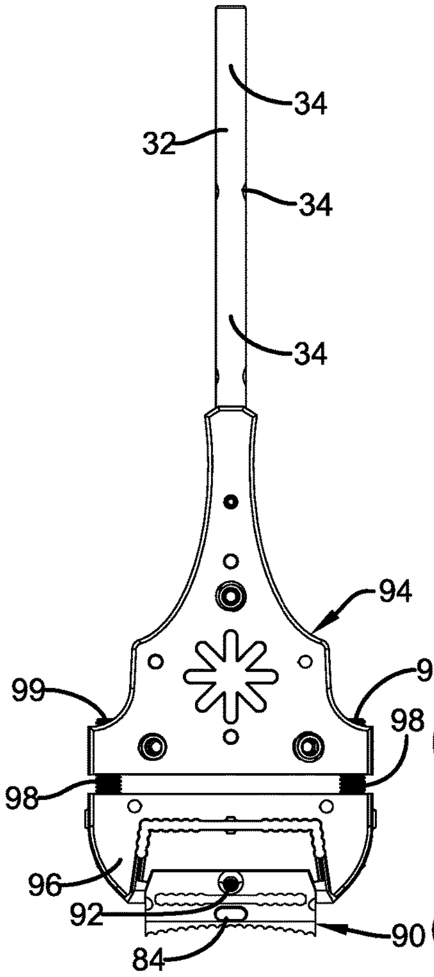
FIGS. 16A-16C and 17A and 17B illustrate front elevation exploded views of the device of FIG. 11A, with 16A-16C and 17A and 17B showing how the talar cutting slot, oblong slot and lower angled fastener holes may be located on a removable talar cutting piece and with FIGS. 16A-16C and 17A-17B showing how the moveable carriage may be moved and tilted.
Figure 16B:
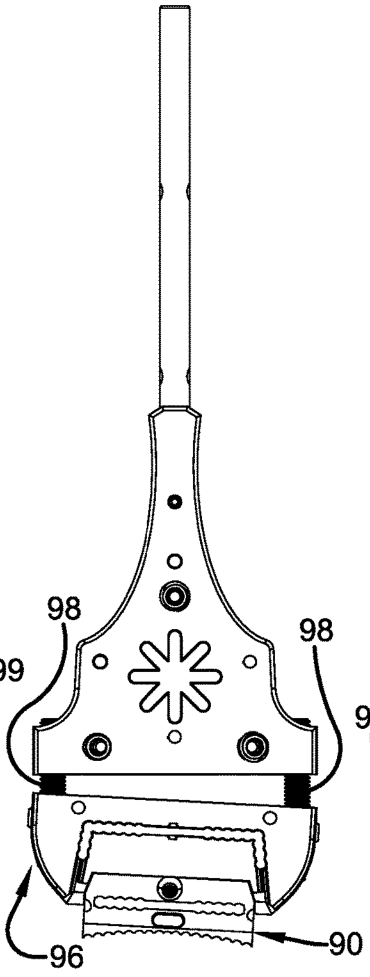
Figure 16C:
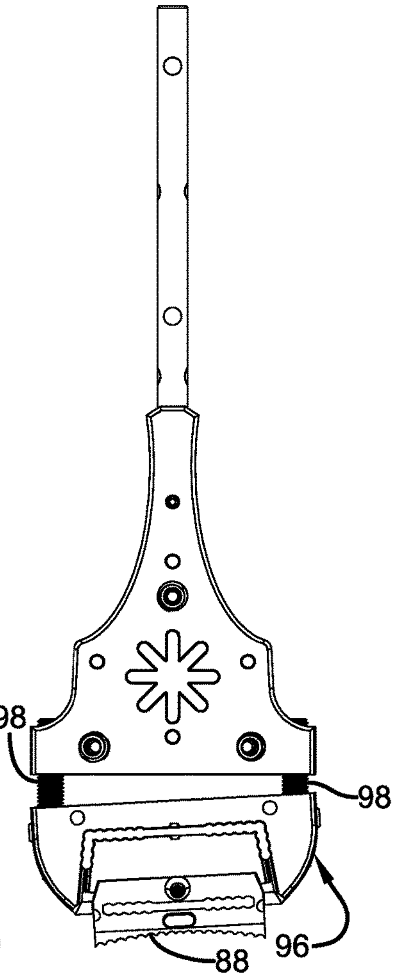
Figure 17A:
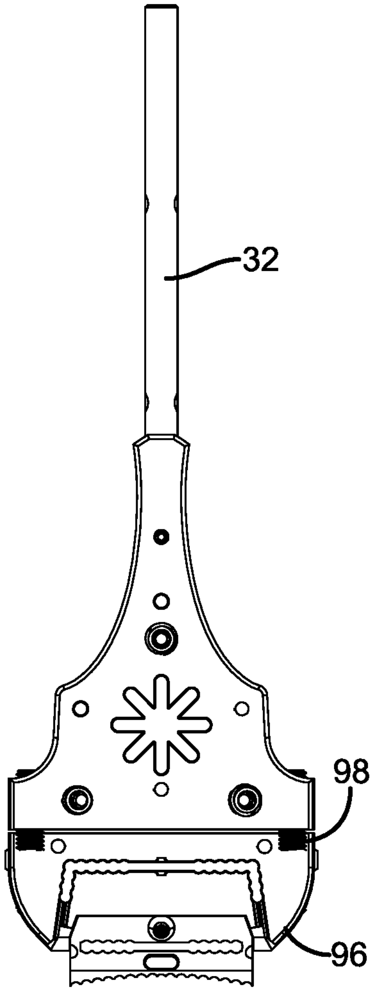
Figure 17B:
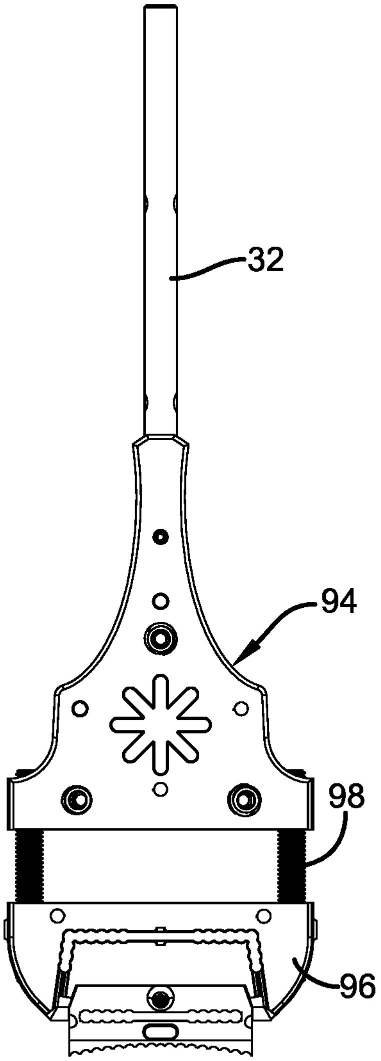

The device 10 may also include at least one angel wing 100. The wing 100 may be used to aid in positioning of the device 10 when irradiated by x-ray. In addition, in the exemplary embodiment, the angel wing 100 comprises at least one bar 102 (e.g., an L-shaped bar 102 with a front portion 102A and a side portion 102B) with at least one prong 104 that may be oriented generally parallel to the device height 22. The prong 104 may extend above and below the side portion 102B and may also progressively increase or decrease in height moving rearwardly. The prong 104 may be radiopaque and may also be used for measuring purposes. The prong 104 may also extend along the side of the user's leg. In the illustrated embodiment, the angel wing 100 is removably but firmly attached to the device body 30 so that when attached the angel wing 100 may be used as a handle to hold the device body 30. For example, the angel wing 100 may include at least one rearwardly extending tab 106 that fits into the tibial cutting slot 70. In addition, optionally, the bar 102 of the angel wing 100 includes at least one wing slot that extends through the tab 106 and is aligned with (and optionally is slightly smaller than) the tibial cutting slot 70 of the device body 30 so that the saw blade may be placed through the wing slot, thus, not requiring removal of the angel wing 100 for cutting of the tibia 36. As shown in FIG. 20, the rear of the tab 106 may include at least one tooth 109 to hold one or more vertically-oriented fasteners. The tab 106 may also include at least one bump 108 to facilitate press fitting into the tibial cutting slot 70 of the device body 30. The prongs 104 may be located to the left 24 and/or right side 26 of the device body 30. For example, in the illustrated embodiment, the angel wing 100 is removable so that it may be flipped, as shown in FIG. 11C, to allow for the surgeon to place the prongs 104 on either side of the device body 30.

As seen in FIGS. 13A-13F, the device 10 may be comprised of a plurality of tools and accessories. For example, in one embodiment the device 10 is comprised of at least one K-wire 130 and/or at least one shoulder pin 128. The K-wire 130 and/or pin 128 can be placed through the device 10 to provide stability and secure the device 10 to any bone during use. At least one screwdriver 122 and/or at least one hex handle driver 126 can be used to fasten, manipulate, tighten, and loosen various components of the device 10. In addition, the device 10 may be comprised of at least one cannulated driver 120 and/or cannulated hex handle driver 124 that can be used to advance or withdraw threaded structures of the device 10 over a wire 130 and/or pin 128. The pin 128 and/or wires 130 can be placed through blade slot teeth 82 of the talar cutting piece 90 to restrict a cutting blade from moving past the pin 128 and/or wire 130. In this manner, the pin 128 and/or wires 130 act as a cutting guard, while also securing the device 10 to the bone. In one embodiment, the talar cutting piece 90 may be comprised of at least one smooth central portion 83.

Figure 24:
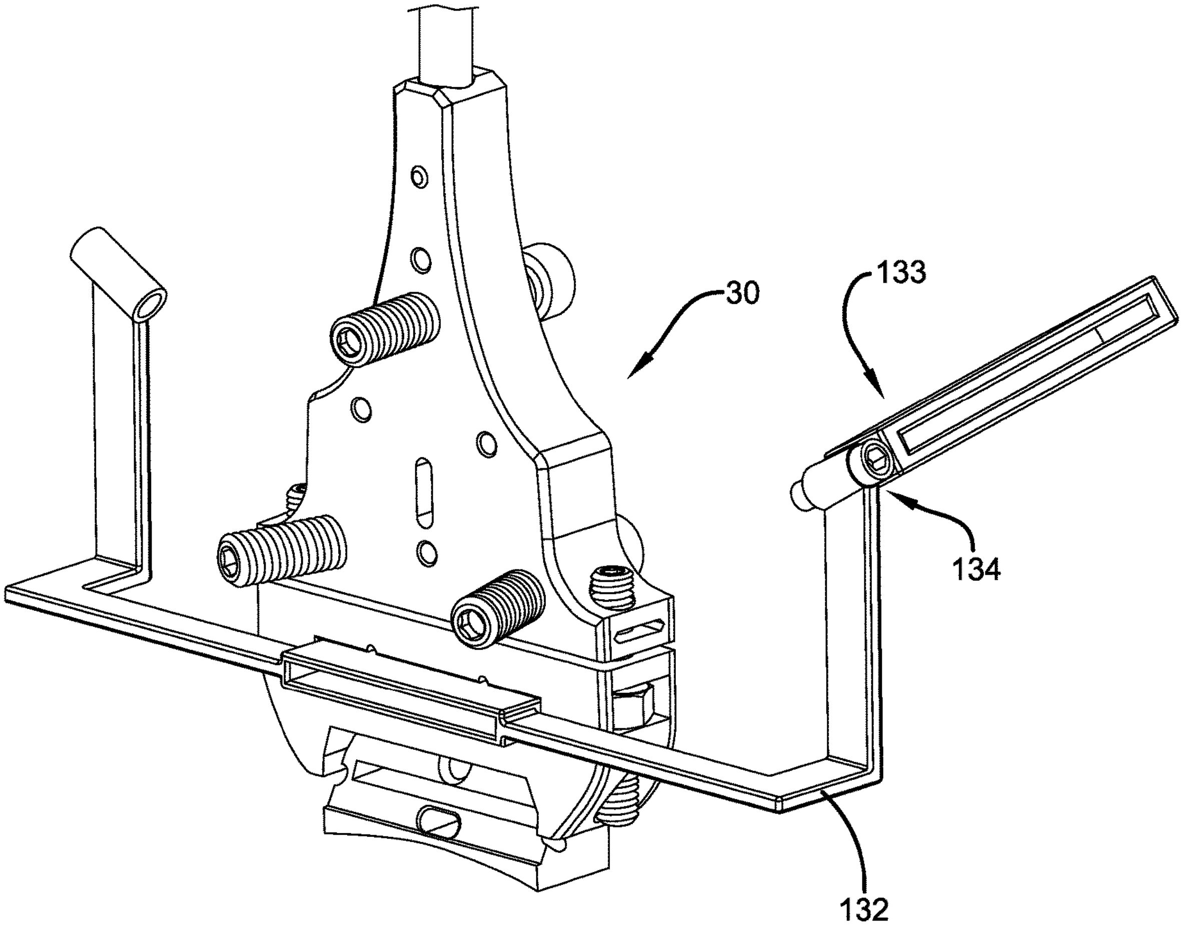
FIG. 24 illustrates a perspective view of a clip of one embodiment of the present invention while attached to the device body.

In one embodiment, the device 10 may be comprised of at least one clip 132, as seen in FIG. 24. The clip 132 may function as an outrigger structure to perform osteotomies of the fibula 37 in conjunction with the tibia 36 and/or talus 38. The clip 132 may be comprised of a cutting slot 133. The slot 133 may be smooth or toothed. Without being bound by any particular theory, the teeth may be sized to hold one or more pins 128 or wires 130 that can be positioned through the cutting slot to provide stability to the device 10. Alternatively, as shown in one embodiment of FIG. 24, the cutting slot 133 may be smooth (without teeth). The cutting slot 133 may be attached to, and removable from clip 132, to allow for attachment to either upright segment of the clip 132. Without being bound by any particular theory, the connection between clip 132 and cutting slot 133 may involve a fastener 134 secured with a cannulated driver 120, screwdriver 122, cannulated hex handle driver 124 or hex handle driver 126."

Certain terms are used throughout the following description and claims to refer to particular features or components. As one skilled in the art will appreciate, different persons may refer to the same feature or component by different names. This document does not intend to distinguish between components or features that differ in name but not structure or function. As used herein "tibial alignment guide and cutting system" and "device" are interchangeable and refer to the tibial alignment guide and cutting system 10 of the present invention.

Notwithstanding the forgoing, the tibial alignment guide and cutting system 10 of the present invention and its various components can be of any suitable size and configuration as is known in the art without affecting the overall concept of the invention, provided that they accomplish the above-stated objectives. One of ordinary skill in the art will appreciate that the size, configuration, and material of the tibial alignment guide and cutting system 10 as shown in the FIGS. are for illustrative purposes only, and that many other sizes and shapes of the tibial alignment guide and cutting system 10 are well within the scope of the present disclosure. Although the dimensions of the tibial alignment guide and cutting system 10 are important design parameters for user convenience, the tibial alignment guide and cutting system 10 may be of any size, shape, and/or configuration that ensures optimal performance during use and/or that suits the user's needs and/or preferences.

Various modifications and additions can be made to the exemplary embodiments discussed without departing from the scope of the present invention. While the embodiments described above refer to particular features, the scope of this invention also includes embodiments having different combinations of features and embodiments that do not include all the described features. Accordingly, the scope of the present invention is intended to embrace all such alternatives, modifications, and variations as fall within the scope of the claims, together with all equivalents thereof.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A tibial alignment guide and cutting system comprising:
- a device body;
- a star-shaped cutout;
- a vertical rod comprised of a rod hole;
- an angled fastener hole;
- a perpendicular fastener hole;
- a screw;
- an upward-angled fastener hole;
- a talar cutting piece comprised of a cutting window and a cutting slot;
- a bar comprised of a prong and a wing tab;
- a tibial cutting slot;
- an angel wing comprised of an angel wing cutting slot; and
- a fastener.

2. The tibial alignment guide and cutting system of claim 1, wherein the vertical rod is comprised of a radiopaque rod.

3. The tibial alignment guide and cutting system of claim 1, wherein the vertical rod is comprised of a bottom end that is connected to the device body.

4. The tibial alignment guide and cutting system of claim 1, wherein the fastener is comprised of a smooth fastener, a threaded fastener, a drill-tipped fastener or a cannulated fastener.

5. A tibial alignment guide and cutting system comprising:
- a device body;
- a cutout comprised of an angled slot;
- a blade slot comprised of a tooth;
- an outrigger clip that attaches to the device body;
- an oblong slot;
- a vertical rod comprised of a first rod hole and a second rod hole;
- a left-angled fastener hole and a right-angled fastener hole;
- a first perpendicular fastener hole, a second perpendicular fastener hole, and a third perpendicular fastener hole;
- a screw;
- an upward-angled fastener hole;
- a talar cutting piece comprised of a cutting window, a cutting slot, an arc-shaped recess comprised of a tooth, and a fastener hole;
- a bar comprised of a prong and a wing tab;
- a tibial cutting slot;
- a moveable carriage that attaches to the device body;
- a driver;
- a pin; and
- a k-wire.

6. The tibial alignment guide and cutting system of claim 5, wherein the driver is comprised of a cannulated driver, a screwdriver, a cannulated hex handle driver, or a hex handle driver.

7. The tibial alignment guide and cutting system of claim 5, wherein the first rod hole is positioned 90 degrees relative to the second rod hole.

8. The tibial alignment guide and cutting system of claim 5, wherein the first perpendicular fastener hole, the second perpendicular fastener hole, and the third perpendicular fastener hole are arranged in a triangular pattern.

9. The tibial alignment guide and cutting system of claim 5, wherein the left-angled fastener hole and the right-angled fastener hole converge.

10. A tibial alignment guide and cutting system comprising:
- a device body comprised of a perpendicular fastener hole and an angled fastener hole;
- a star-shaped cutout;
- a blade slot comprised of a tooth;
- an outrigger clip that attaches to the device body;
- a vertical rod comprised of a rod hole;
- a screw;
- an upward-angled fastener hole;
- a talar cutting piece comprised of a talar cutting window, a talar cutting slot, an oblong slot, a blade slot, an arc-shaped recess comprised of a tooth, and a fastener hole;
- a bar comprised of a prong and a wing tab;
- a tibial cutting slot positioned above the talar cutting slot;
- an angel wing comprised of an angel wing cutting slot; and
- a moveable carriage that attaches to the device body.

11. The tibial alignment guide and cutting system of claim 10, wherein the device body is comprised of a transparent device body.

12. The tibial alignment guide and cutting system of claim 10, wherein the device body is comprised of a radiolucent device body.

13. The tibial alignment guide and cutting system of claim 10, wherein the perpendicular fastener hole extends from a front face of the device body to a rear face of the device body.

14. The tibial alignment guide and cutting system of claim 13, wherein the perpendicular fastener hole is perpendicular to a width of the device body.

15. The tibial alignment guide and cutting system of claim 10, wherein the angled fastener hole extends from a front face of the device body to a rear face of the device body.

16. The tibial alignment guide and cutting system of claim 15, wherein the angled fastener hole extends from a front face of the device body to a rear face of the device body at an angle between 10 and 80 degrees relative to a width of the device body and inwardly.

17. The tibial alignment guide and cutting system of claim 10, wherein the tibial cutting slot extends from a front face of the device body to a rear face of the device body.

18. The tibial alignment guide and cutting system of claim 10, wherein the talar cutting piece removably attaches to the device body.

19. The tibial alignment guide and cutting system of claim 10, wherein the movable carriage attaches to the device body via a vertical fastener.

20. The tibial alignment guide and cutting system of claim 10, wherein the angel wing is comprised of an L-shaped bar.

* * * * *